(12) United States Patent
Dawson

(10) Patent No.: US 8,678,005 B2
(45) Date of Patent: Mar. 25, 2014

(54) ADJUSTABLE TRACHEOSTOMY VALVE

(75) Inventor: Randy J. Dawson, Waterford, PA (US)

(73) Assignee: Dawson Medical Technologies LLC, Waterford, PA (US)

( * ) Notice: Subject to any disclaimer, the term of this patent is extended or adjusted under 35 U.S.C. 154(b) by 427 days.

(21) Appl. No.: 13/109,137

(22) Filed: May 17, 2011

(65) Prior Publication Data

US 2012/0097170 A1 Apr. 26, 2012

Related U.S. Application Data

(60) Provisional application No. 61/407,014, filed on Oct. 26, 2010.

(51) Int. Cl.
*A62B 9/02* (2006.01)
*A61M 16/20* (2006.01)

(52) U.S. Cl.
USPC ............ 128/207.16; 128/205.24; 128/207.14; 137/512.15; 251/205; 251/208

(58) Field of Classification Search
USPC ............ 128/203.11, 205.24, 207.14–207.16; 137/102, 512.15; 251/205, 208, 297
See application file for complete search history.

(56) References Cited

U.S. PATENT DOCUMENTS

| | | | |
|---|---|---|---|
| 3,263,684 A | 8/1966 | Bolton | |
| 4,538,607 A | 9/1985 | Saul | |
| 4,538,620 A * | 9/1985 | Nowacki et al. | 600/538 |
| 4,582,058 A | 4/1986 | Depel et al. | |
| 4,739,987 A * | 4/1988 | Nicholson | 482/13 |
| 4,759,356 A | 7/1988 | Muir | |
| 4,770,413 A * | 9/1988 | Green | 482/13 |
| 4,877,025 A | 10/1989 | Hanson | |
| 5,027,811 A | 7/1991 | Tuxill | |
| 5,059,208 A | 10/1991 | Coe et al. | |
| 5,392,775 A | 2/1995 | Adkins, Jr. et al. | |
| 5,445,145 A | 8/1995 | Redmon | |

(Continued)

FOREIGN PATENT DOCUMENTS

| | | |
|---|---|---|
| GB | 2153976 A | 8/1985 |
| WO | WO 02/34322 A2 | 5/2002 |
| WO | WO 03/061531 A2 | 7/2003 |

OTHER PUBLICATIONS

International Search Report and Written Opinion, Feb. 21, 2012, in PCT/US2011/057661.

(Continued)

*Primary Examiner* — Justine Yu
*Assistant Examiner* — Timothy Stanis
(74) *Attorney, Agent, or Firm* — Thomas & Karceski, PC

(57) ABSTRACT

A valve, usable in connection with a tracheostomy tube, permits phonation by selectively blocking passage of air therethrough. The valve includes a main body portion with first and second internal passages. A first aperture extends radially through a peripheral wall, connecting the first internal passage to an environment external to the main body. A second aperture extends radially through the peripheral wall, connecting the second internal passage to the environment. A trach body portion defines a third internal passage and is connected to the main body portion. A flapper valve is sandwiched between the main body portion and the trach body portion. First and second adjustment rings permit adjustment of opening defined by the first and second apertures, thereby permitting control over the air passing through the first and second apertures.

20 Claims, 17 Drawing Sheets

(56) References Cited

U.S. PATENT DOCUMENTS

| | | | |
|---|---|---|---|
| 5,666,950 A | 9/1997 | Smith | |
| 6,083,141 A * | 7/2000 | Hougen | 482/13 |
| 6,189,534 B1 | 2/2001 | Zowtiak et al. | |
| 6,193,751 B1 * | 2/2001 | Singer | 623/9 |
| 6,358,222 B1 | 3/2002 | Grundei | |
| 6,588,428 B2 | 7/2003 | Shikani et al. | |
| 6,789,542 B1 | 9/2004 | Bischoff | |
| 6,802,316 B1 | 10/2004 | Fulgham | |
| 6,874,752 B2 * | 4/2005 | Jørgensen | 251/205 |
| 7,021,314 B1 | 4/2006 | Lane | |
| 7,025,784 B1 | 4/2006 | Blom et al. | |
| 7,063,086 B2 * | 6/2006 | Shahbazpour et al. | 128/205.24 |
| 7,240,676 B2 | 7/2007 | Rutter | |
| 2003/0226562 A1 | 12/2003 | Schmidt | |
| 2004/0089291 A1 | 5/2004 | Persson | |
| 2006/0260703 A1 | 11/2006 | Johnson | |
| 2009/0032028 A1 | 2/2009 | Bare et al. | |
| 2009/0095302 A1 | 4/2009 | Blom | |

OTHER PUBLICATIONS

Page from Hammacher Schlemmer catalog showing "Respiratory Exerciser," Apr. 2011, p. 46.

* cited by examiner

ADJUSTABLE TRACHEOSTOMY VALVE

CROSS-REFERENCE TO RELATED APPLICATION(S)

This United States Non-Provisional Utility patent application relies for priority on U.S. Provisional Patent Application Ser. No. 61/407,014, filed on Oct. 26, 2010, the contents of which are incorporated herein in their entirety.

FIELD OF THE INVENTION

The present invention concerns a tracheostomy valve. More specifically, the present invention concerns a tracheostomy valve that provides adjustability for both inspiratory and expiratory air flows.

DESCRIPTION OF THE RELATED ART

Numerous examples of tracheostomy valves (also referred to as tracheotomy valves) are known in the art.

One common type of conventional tracheostomy valve permits inspiratory air to enter the tracheostomy tube to which the valve is connected, while blocking expiratory air from exiting through the valve. In so doing, valves of this type direct the expiratory flow through the patient's vocal cords and out of the patient's mouth. These types of valves also are referred to as phonating valves, because they force air through the vocal cords, permitting the person to speak during exhalation without having to plug the tracheostomy tube manually.

It is known, however, that conventional tracheostomy valves of this type are not configured for providing adjustability of either the inspiratory or expiratory flows. Moreover, valves of this type do not permit simulation of different tracheostomy tube sizes.

The lack of adjustability in prior art tracheostomy valves greatly limits patient outcomes and creates a situation of "all or nothing" compliance because the patient can either tolerate the particular phonating valve, or they cannot.

A number of conventional tracheostomy valve constructions are illustrated and described in various U.S. patents and published applications. The following provides a summary of selected prior art references, which are representative of the prior art as a whole.

U.S. Pat. No. 7,240,676 (hereinafter "the '676 patent") describes a tracheotomy valve unit 10 with a valve base 14, support 16, diaphragm 18, and rivet 20 containing a slit valve 21. (The '676 patent at col. 4, lines 50-52.) When a patient inhales, the diaphragm 18 opens and allows air to flow through air ports 30. (The '676 patent at col. 7, lines 11-12.) When the patient exhales, the diaphragm 18 closes and the first valve blocks airflow from the tube, thereby causing the air to be forced past the person's larynx and epiglottis, toward the person's mouth and nose. (The '676 patent at col. 7, lines 14-18.) When the intrathoracic pressure during expiration exceeds 12 cm of water, the second valve, i.e., the slit valve 21, opens to permit airflow back through the valve unit 10. (The '676 patent at col. 7, lines 19-23.) The operation of the slit valve 21, therefore, improves comfort and allows the person to tolerate the speaking valve. (The '676 patent at col. 7, lines 26-30.)

U.S. Pat. No. 6,802,316 (hereinafter "the '316 patent") describes a tracheostomy valve 10 that is a unidirectional valve allowing a user to inhale through the valve 10, while preventing the exhalation of air through the same valve 10, thereby permitting speech. (The '316 patent at col. 4, lines 53-56.) The tracheostomy valve 10 includes a valve body 12 with a flapper valve 24 therein. (The '316 patent at col. 4, lines 57-58.)

U.S. Pat. No. 6,358,222 (hereinafter "the '222 patent") describes a shunt valve for insertion into a surgical canal between the trachea and the esophagus. (The '222 patent at col. 3, lines 3-6.) The device includes a flap regulator valve 2 to permit air to pass through the device in one direction. (The '222 patent at col. 3, lines 9-15.)

U.S. Pat. No. 5,445,145 (hereinafter "the '145 patent") describes an apparatus to manually open and close a shutter-like device for tracheostomy patents to facilitate breathing. Specifically, the '145 patent describes a device 10 with a shutter box 12. (The '145 patent at col. 4, lines 50-51.) The shutter box 12 may be actuated by the person's fingers without touching the device connected to the tracheostomy. (The '145 patent at col. 5, lines 51-58.)

U.S. Pat. No. 5,392,775 (hereinafter "the '775 patent") describes a duckbill valve for a tracheostomy tube that permits speech. The valve 10 includes a one-way valve 16 (i.e., a duckbill valve) within the valve housing 14. (The '775 patent at col. 3, lines 46-49.) The valve 16 opens when the person inhales. (The '775 patent at col. 4, lines 7-12.) When the person exhales, the valve 16 closes. (The '775 patent at col. 4, lines 1-7.) If the exhalation pressure is very high (such as when the person coughs), the valve 16 may invert to relieve the pressure. (The '775 patent at col. 4, lines 25-30.)

U.S. Pat. No. 4,759,356 (hereinafter "the '356 patent") describes a tracheostomy valve unit 10 with a diaphragm 18. (The '356 patent at col. 7, lines 63-66.) The diaphragm 18 permits inhaled air to pass through the valve 10 while also prohibiting exhaled air from passing through the valve 10. (The '356 patent at col. 10, lines 24-30.)

U.S. Patent Application Publication No. 2009/0032028 (hereinafter "the '028 Application") describes a tracheostomy valve with 30 with a diaphragm 38. (The '028 Application at paragraph [0035].) As is apparent, inhalation causes the diaphragm 28 to bend, permitting air flow. Exhalation, however, applies pressure to the diaphragm 38 to close the valve 30.

The content of each of the U.S. references discussed above are incorporated herein by reference in their entirety.

As should be apparent, none of the valves known to the art provide adjustability of the valves, as noted above.

More specifically, the valves described in the prior art lack adjustability of either inhalation or exhalation aspects of the valves.

Still other deficiencies in the prior art should be apparent to those skilled in the art.

SUMMARY OF THE INVENTION

The present invention seeks to address one or more deficiencies in tracheostomy valves and devices that are known in the prior art.

Unlike the conventional tracheostomy valves, one embodiment of the tracheostomy valve of the present invention provides adjustability for at least one of inhalation or expiration.

Another embodiment offers adjustability for both inhalation and exhalation, via an adjustment feature that provides either infinite or finite adjustment positions.

Due at least in part to the adjustability aspect of the present invention and its intended use, the valve of the present invention also is referred to as an adjustable tracheostomy weaning and phonating valve.

In one contemplated context, the valve of the present invention allows the practitioner to slowly and selectively exercise and evaluate the physiology of the human upper airway, including the vocal cords and epiglottis, to allow decannulation of a tracheostomy.

An embodiment of the adjustable tracheostomy weaning and phonating valve allows medical personnel to adjust both the inspiratory as well as the expiratory flows through the tracheostomy tube, allowing full control of the weaning process from the tracheostomy tube.

An embodiment of the adjustable tracheostomy weaning and phonating valve also allows the practitioner to easily and quickly simulate a smaller tracheostomy tube prior to placement in a patient to evaluate whether the patient can tolerate a change in the tracheostomy tube size and, if necessary, quickly revert to the equivalent of a larger tracheostomy tube.

One embodiment of the present invention provides a valve that includes a main body portion with a peripheral wall defining an interior space and an internal wall separating the internal space into first and second internal passages, a first aperture extending radially through the peripheral wall, connecting the first internal passage to an environment external to the main body, and a second aperture extending radially through the peripheral wall, connecting the second internal passage to the environment. The valve also includes a trach body portion disposed adjacent to the main body portion. The trach body portion defines a third internal passage. A flapper valve is sandwiched between the main body portion and the trach body portion. A first adjustment ring is includes that has a third aperture therethrough. The first adjustment ring is disposed on the main body portion so that the third aperture is in register with the first aperture. The first adjustment ring is movable with respect to the main body portion to permit alteration of the positional relationship between the first and third apertures to alter a size of a first opening defined by the first and third apertures. The valve also includes a second adjustment ring having a fourth aperture therethrough. The second adjustment ring is disposed on the main body portion so that the fourth aperture is in register with the second aperture. The second adjustment ring is movable with respect to the main body portion to permit alteration of the positional relationship between the second and fourth apertures to alter a size of a second opening defined by the second and fourth apertures.

In one contemplated embodiment of the present invention, the first adjustment ring is rotatable with respect to the main body portion between an opened position, where the first and third apertures are aligned to permit a maximum air flow therethrough, and a closed position where the first and third apertures are not aligned to prevent air flow therethrough. The second adjustment ring is rotatable with respect to the main body portion between an opened position, where the second and fourth apertures are aligned to permit a maximum air flow therethrough, and a closed position where the second and fourth apertures are not aligned to prevent air flow therethrough.

In another contemplated embodiment, the first and second adjustment rings are adjustable to a predetermined number of discrete adjustment positions between the opened and closed positions.

Alternatively, the first and second adjustment rings are adjustable in any of an infinite number of adjustment positions between the opened and closed positions.

Still further, the present invention is directed to a valve with a coupling ring disposed around a bottom end of the main body portion and a top end of the trach body portion, connecting the main body portion to the trach body portion so that the main body portion and the trach body portion do not rotate with respect to one another. In this embodiment, a cap is disposed at a top end of the main body portion such that the cap does not rotate with respect to the main body portion.

An embodiment of the present invention includes a cap with a closed end, thereby requiring air passing through the first and second internal passages to flow through the first and second apertures.

Another embodiment of the present invention includes a cap with a coupling portion permitting coupling of the main body portion to a ventilator.

The present invention also encompasses a valve with at least one first protrusion disposed on a bottom edge of the cap for engagement with at least one first notch disposed along a top edge of the first adjustment ring to secure the first adjustment ring in a first predetermined position. In this embodiment, at least one second protrusion is disposed on a top edge of the coupling ring for engagement with at least one second notch disposed along a bottom edge of the second adjustment ring to secure the second adjustment ring in a second predetermined position.

It is contemplated that, in the valve of the present invention, there may be a plurality of first notches, permitting the first adjustment ring to be secured in a plurality of first predetermined positions. Moreover, the valve may be provisioned with a plurality of second notches, permitting the second adjustment ring to be secured in a plurality of second predetermined positions.

The plurality of notches for the first and second notches may be limited to six in number, permitting the first and second adjustment rings to be secured in six predetermined positions corresponding to six tracheostomy tube sizes.

If six notches are used, the notches may correspond to six tracheostomy tube sizes including 10 mm, 8, mm, 6, mm, 4 mm, 2 mm, and 0 mm sizes.

It is contemplated that the valve of the present invention may include a biasing element disposed between the first and second adjustment rings, biasing the first adjustment ring into engagement with the cap and also biasing the second adjustment ring into engagement with the coupling ring.

The biasing element may be a spring ring.

If a spring ring is employed, it is contemplated that the spring ring will include a plurality of undulations and a plurality of flat surfaces, alternate ones of the flat surfaces being in contact with the first and second adjustment rings, respectively.

The valve of the present invention also may include a first valve stop disposed within the first internal passage, adjacent to the flapper valve, and a second valve stop disposed within the third internal passage adjacent to the flapper valve.

Where valve stops are included, the first valve stop may cooperate with the flapper valve to permit air to flow through the first internal passage into the third internal passage during inhalation but prevents air from flowing from the third internal passage to the first internal passage during exhalation. Similarly, the second valve stop may cooperate with the flapper valve to permit air to flow through the second internal passage from the third internal passage during exhalation but prevents air from flowing from the second internal passage to the third internal passage during inhalation.

In one contemplated embodiment of the valve of the present invention, the first and second internal passages have substantially equal cross-sectional areas and the third internal passage has a cross-sectional area that is at least equal to the sum of the cross-sectional areas of the first and second internal passages.

In another contemplated embodiment, the flapper valve is made from silicone rubber.

It is contemplated that the trach body portion is connectable to a tracheostomy tube.

In addition, the valve of the present invention is contemplated to facilitate phonation for a person by restricting exhalation air therethrough, thereby forcing at least a portion of the exhalation air through the person's vocal chords.

Still other aspects of the present invention will be made apparent from the instant disclosure and will be apparent to those skilled in the art.

BRIEF DESCRIPTION OF THE DRAWINGS

The present invention will now be described in connection with the drawings appended hereto, in which.

DETAILED DESCRIPTION OF EMBODIMENT(S) OF THE INVENTION

The present invention will now be described in connection with one or more embodiments thereof. It is noted that specific focus on any of described embodiments is intended to be exemplary of the breadth and scope of the present invention. Therefore, the discussion of specific embodiments should not be understood to be limiting of the present invention. To the contrary, after appreciating the details that are provided herein, those skilled in the art will readily appreciate that there are variations and equivalents of the embodiments described herein that may be employed without departing from the scope of the present invention.

In addition, the present invention will be described in connection with the contemplated use as a valve for a tracheostomy. While described in this context, it is possible that the valve of the present invention might be employed in other environments. Therefore, use of the invention in another environment (in addition to a tracheostomy) also is intended to fall within the scope of the present invention and should not be considered as a departure from the present invention.

Next, the description of the present invention includes the discussion of various materials that may be used to construct one or more elements of the valve of the present invention. The listed materials are intended to be exemplary of the types of materials that may be employed for the construction of the present invention. As should be apparent to those skilled in the art, however, other materials may be substituted without departing from the scope of the present invention. Moreover, there is no particular material that is contemplated to be critical for any particular element of the present invention. As a result, alternative materials are intended to be encompassed by the scope of the present invention.

It should be understood that the discussion of any one element, part or component of one embodiment of the present invention may be applicable to similar parts, elements, or components of other embodiments. Moreover, as should be apparent to those skilled in the art, aspects of one element, part, or component of the embodiments of the present invention may be applicable to other aspects of the present invention.

Figure 1:
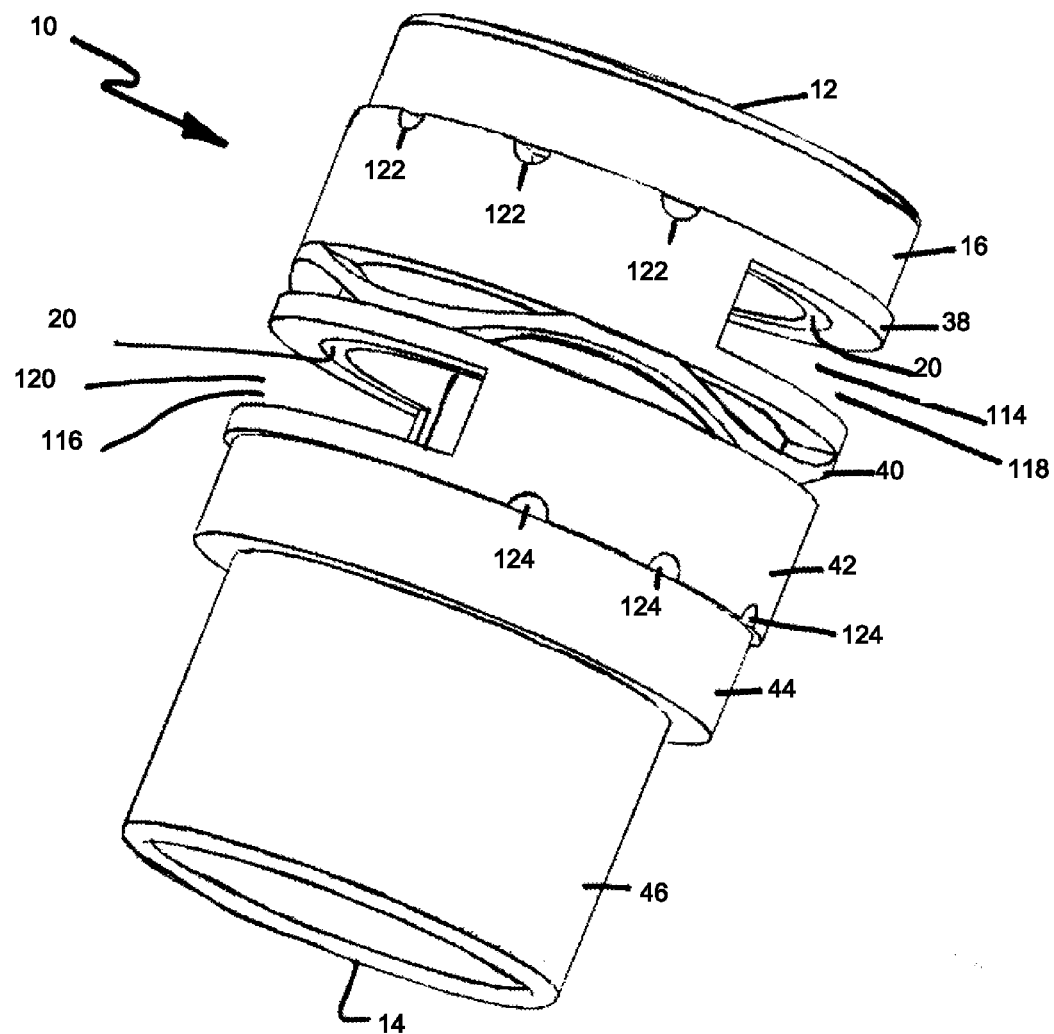
FIG. 1 is a perspective, side view of one contemplated embodiment of the tracheostomy valve of the present invention, illustrating the relative positions of various elements of the valve with respect to one another.
Figure 2:
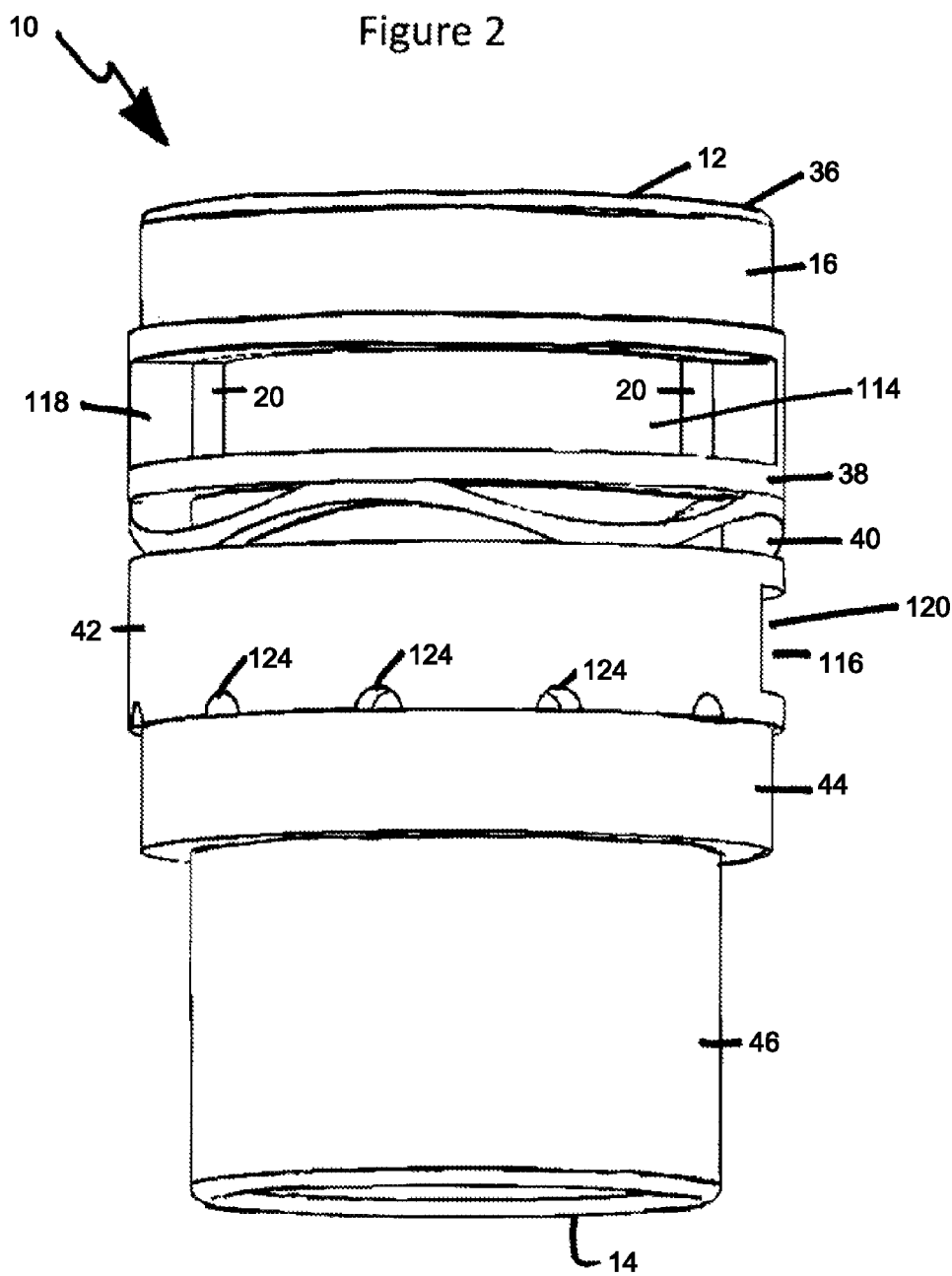
FIG. 2 is a front view of the tracheostomy valve illustrated in FIG. 1.
Figure 3:
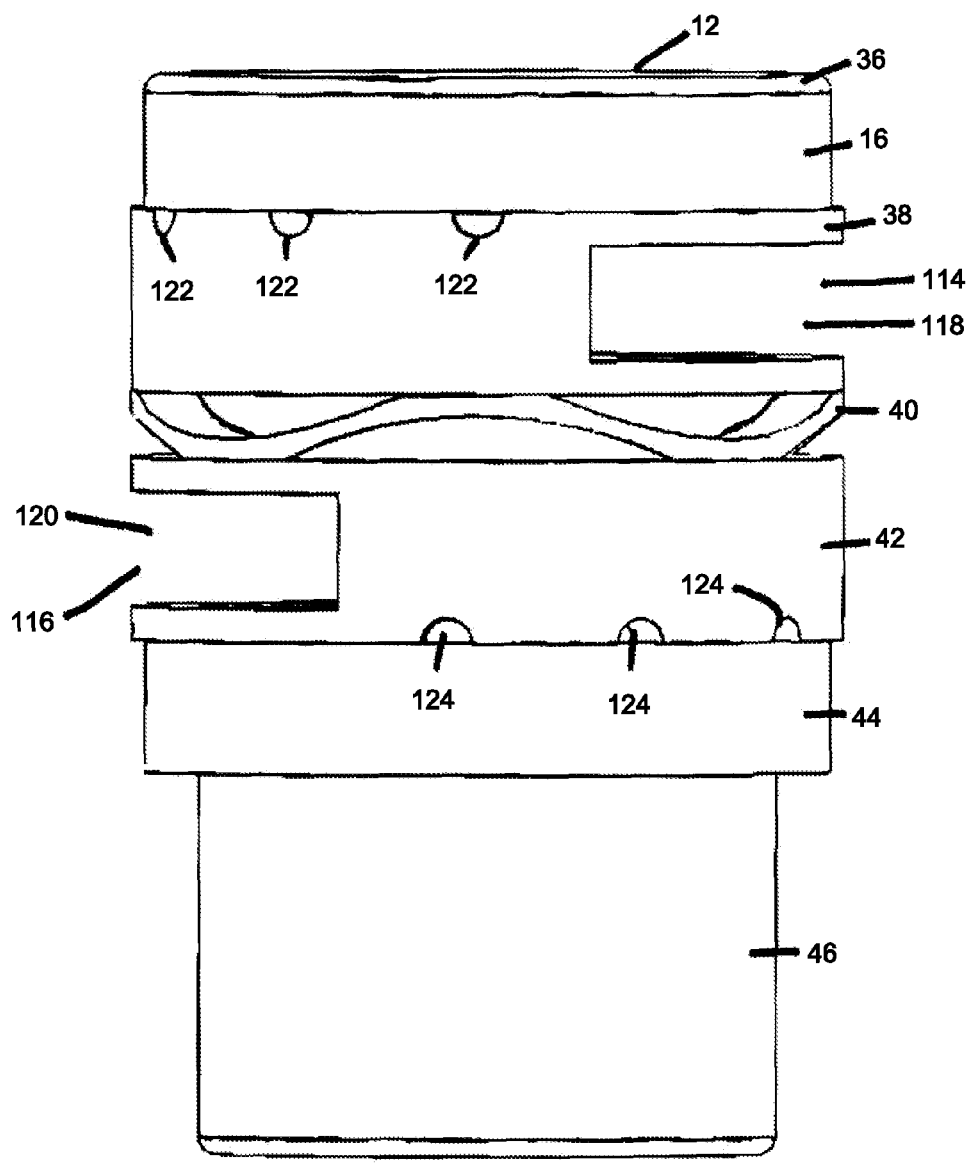
FIG. 3 is a left side view of the valve shown in FIG. 1.

FIG. 1 is a side view of a first embodiment of the tracheostomy valve 10 of the present invention. For brevity, the tracheostomy valve 10 also is referred to herein as the "valve 10."

The valve 10 includes several components, many of which are visible in FIG. 1. Details concerning the various elements of the valve 10 are provided in connection with the remaining figures appended hereto.

The valve 10 is essentially a cylindrical device. While a cylindrical construction is contemplated for the valve 10 of the present invention, any other suitable shape may be employed without departing from the scope of the present invention. For example, the valve 10 may present an oval, elliptical, square, triangular, polygonal, or amorphous cross-section, among others. The exact shape and size of the valve 10 is not critical to the present invention. Therefore, the present invention is not contemplated to be limited to any particular shape or size.

Referring to FIG. 1, the valve 10 defines a top end 12 (or a distal end 12) and a bottom end 14 (or a proximal end 14). The top or distal end 12 is intended to be exposed to the environment. The bottom or proximal end 14 is intended to be inserted into a suitable tracheostomy tube (not shown) that is inserted through the tracheostomy in a person's neck. The valve 10 may be either permanently attached to the tracheostomy tube or may be removably attached thereto. While anticipated to be removable, it is not necessary for the valve 10 to be removable from the tracheostomy tube to practice the present invention.

At its top end 12, the valve 10 includes a cap 16. The cap 16 has a closed structure so that the cap 16 closes off the top end 12 of the valve 10 when inserted thereon. The cap 16 may be attached to the top end 12 of the valve 10 in a removable or a non-removable fashion. The cap 16 may, for example, be press-fitted onto the top end 12 of the valve 10. Alternatively, the cap 16 may threadedly engage the top end 12 of the valve 10. Other attachment means are contemplated and are intended to fall within the scope of the present invention. While the cap 16 is contemplated to be removable from the valve 10, the removability of the cap 16 is not critical to the construction, operation, or use of the present invention.

The cap 16 is contemplated to be made from a suitable material that includes, but is not limited to, plastics, metals, ceramics, and composite materials. In one anticipated embodiment, the cap 16 is made from a plastic material. Plastic is one preferred material because it reduces the weight of the cap 16. In addition, plastic materials are easily cleaned by submersion in water or a suitable cleaning solution, which facilitates hygienic handling of the cap 16 and the valve 10. Additionally, plastic is a flexible material, which permits a snap-fit closure for the valve 10, as detailed below. Other reasons for selecting plastic should be apparent to those skilled in the art.

While the embodiment of the cap 16 is shown as having a closed end, it is contemplated that the cap 16 need not be entirely closed. It is possible that the cap 16 might include one or more apertures that permit ingress and egress of air therethrough. In other words, it is not necessary for the cap 16 to provide a completely closed end to practice the present invention.

In one contemplated embodiment, the cap 16 may incorporate a filter material therein. The filter material is expected to filter out any materials from the environment, such as dust, pollen, etc., thereby reducing the possibility of any allergic reactions from the person wearing the valve 10 of the present invention.

Figure 4:
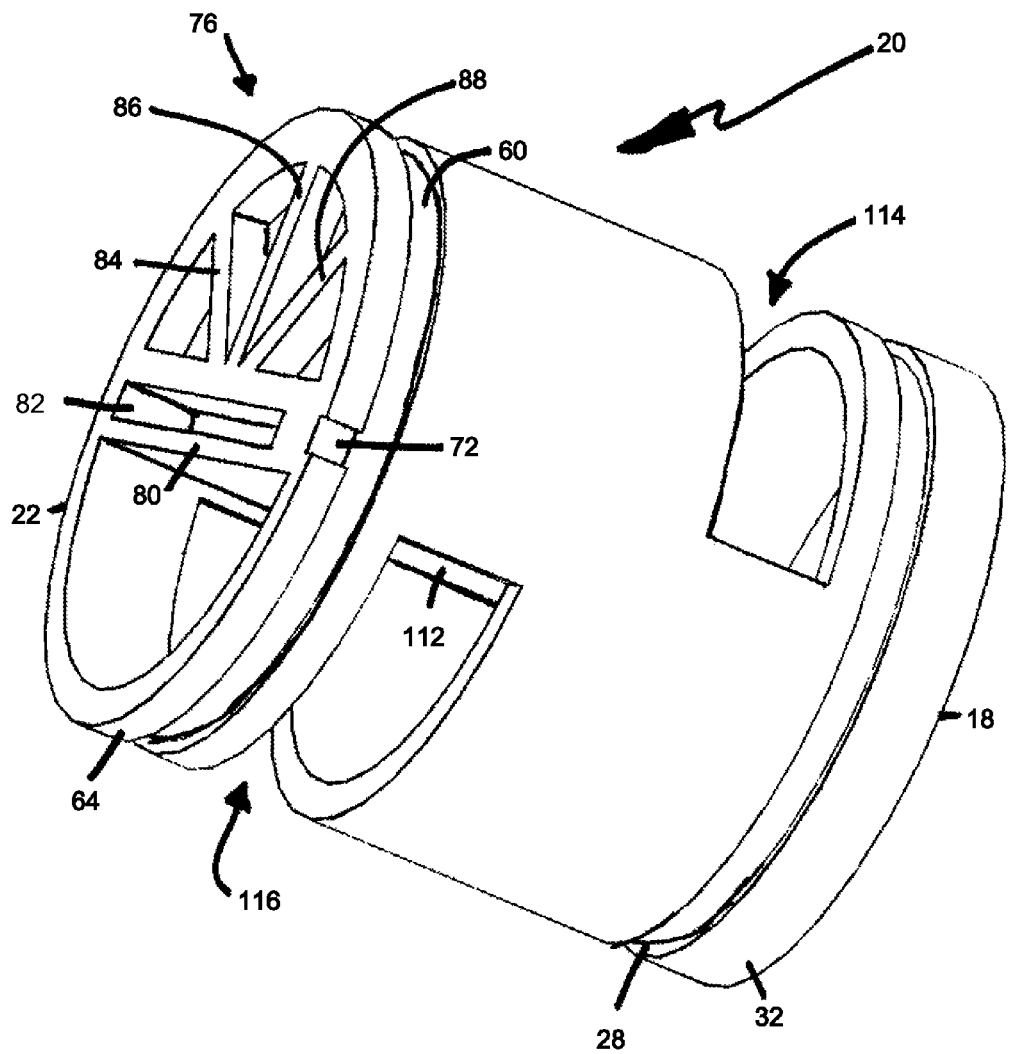
FIG. 4 is a perspective, bottom view of the main barrel portion of the tracheostomy valve illustrated in FIG. 1.
Figure 5:
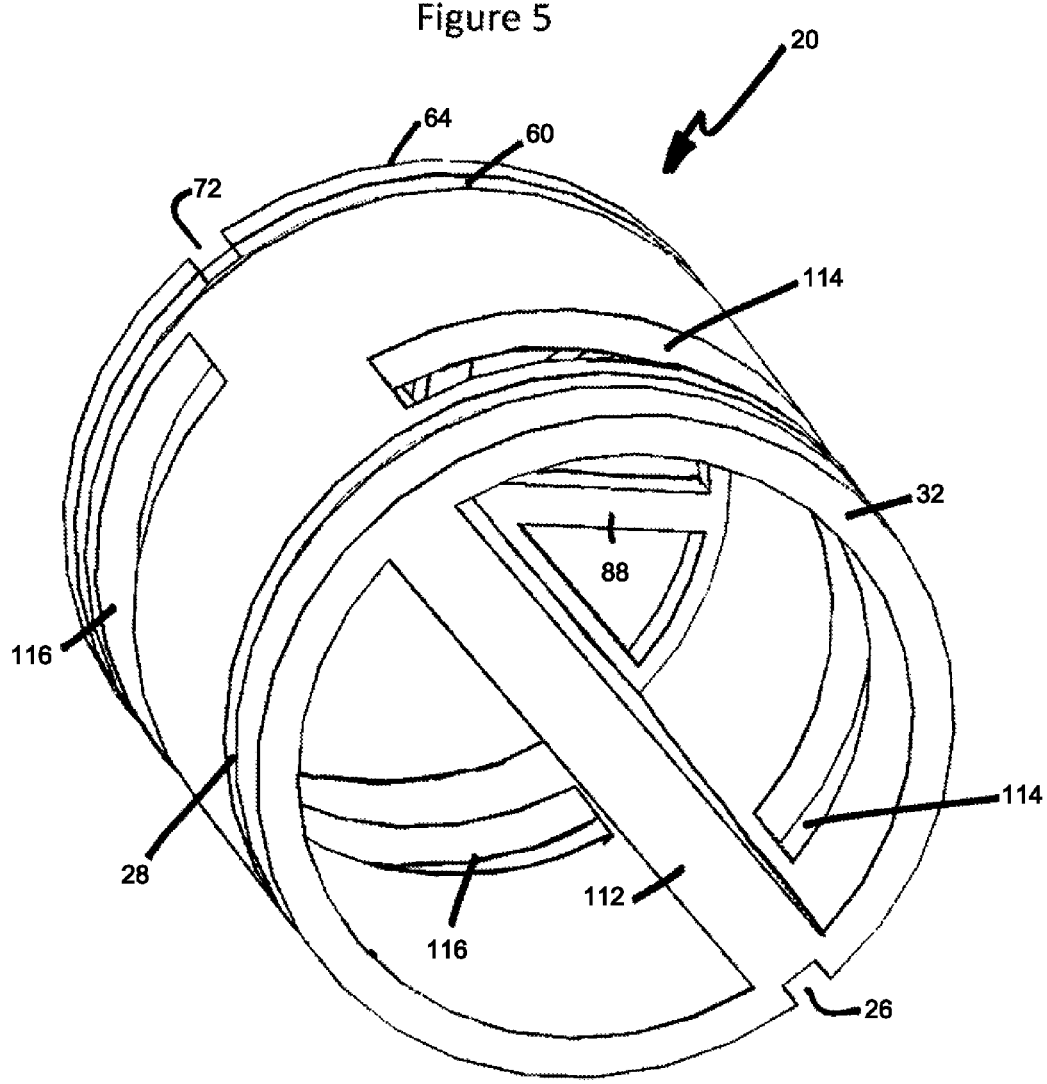
FIG. 5 is a perspective, top view of the main barrel portion illustrated in FIG. 4.

The cap 16 is contemplated to fit snugly over the top (or distal) end 18 of the main barrel 20, which is illustrated in detail in FIGS. 4 and 5. The cap 16 is contemplated to be snap-fit onto the top end 18 of the main barrel 20 such that the cap 16 cannot rotate with respect to the main barrel 20. The bottom (or proximal end) end 22 of the main barrel 20 is designated for ease of reference.

Figure 10:
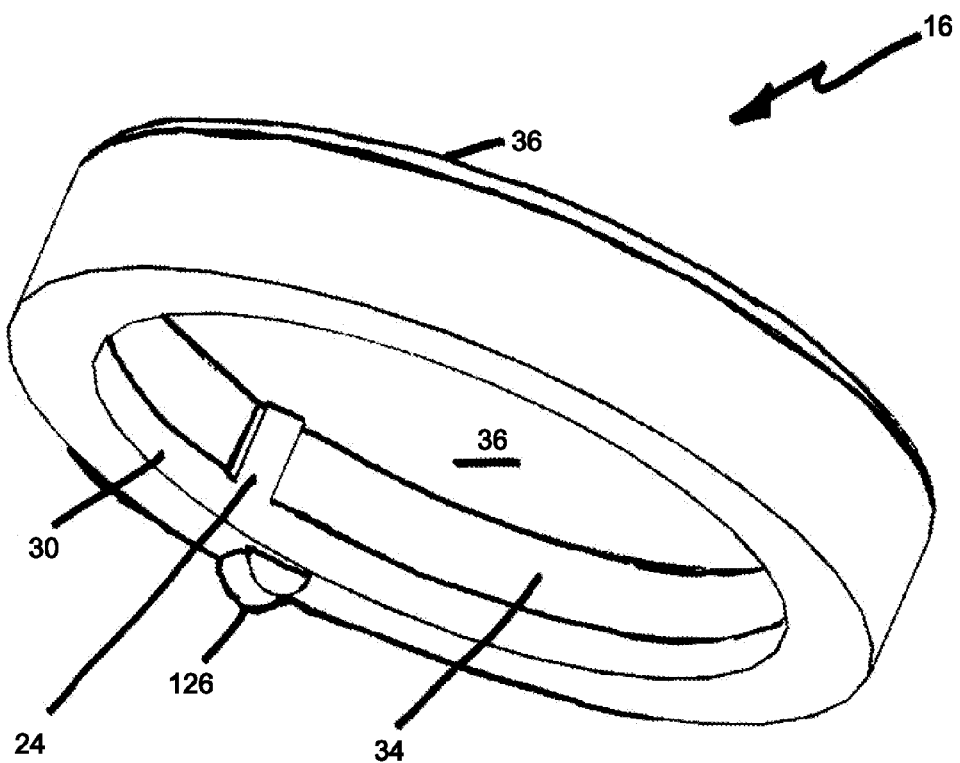
FIG. 10 is a perspective, bottom view of the cap portion of the tracheostomy valve illustrated in FIG. 1.

With reference to FIG. 10, it is noted that the cap 16 includes a locating ridge 24 on an interior surface. The locating ridge 24 is intended to fit into the locating recess 26 on the main barrel 20 so that the cap 16 does not rotate with respect to the main barrel 20. As also should be apparent, the main barrel 20 includes a locating channel 28 adjacent to the top end 18. The locating channel 28 receives the locating ring 30, which is provided on the interior perimeter of the cap 16.

As noted above, the cap 16 is intended to be constructed from a suitably flexible material so that the cap 16 may be press-fit onto the top end 18 of the main barrel 20 such that the locating ring 30 engages the locating channel 28.

As also should be apparent, the main barrel 20 includes a locating ring 32 that engages a locating channel 34 on the interior of the cap 16. The locating rings 30, 32 and locating channels 28, 34 cooperate to retain the cap 16 on the main barrel 20.

As a point of reference, the closed end 36 of the cap 16 is illustrated in FIG. 10. As noted above, the closed end 36 may include a filter or alternative structure, as may be required or desired. In addition, the closed end 36 also may accommodate a relief valve (or other suitable structure) that permits relief of over pressure that may occur, for example, if the wearer coughs.

With continued reference to the engagement between the cap 16 and the main barrel 20, it is noted that cap 16 may be affixed to the top end 18 of the main barrel 20 via any other suitable connection. In other words, it is not required that the connection rely on the locking rings 30, 32 and locking channels 28, 34 to practice the present invention. Moreover, a plurality of locating ridges 24 and locating recesses 26 may be employed, as desired or as required.

Returning to FIG. 1, the valve 10 also includes a first adjustment ring 38 located adjacent to the cap 16. A spring ring 40 is positioned adjacent to the first adjustment ring 38. A second adjustment ring 42 is positioned adjacent to the spring ring 40. Coupling ring 44 is disposed adjacent to the second adjustment ring 42. A trach barrel 46 is positioned adjacent to the coupling ring 44.

Figure 7:
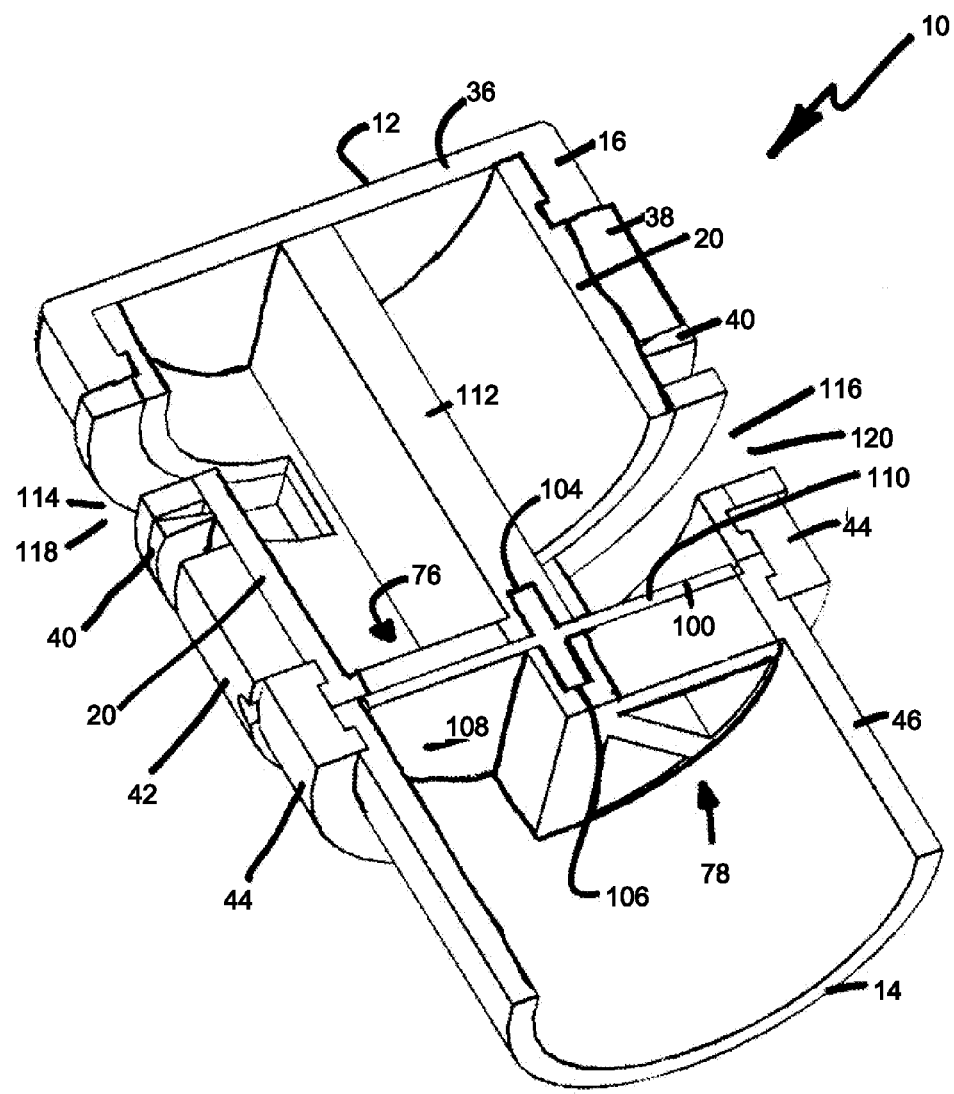
FIG. 7 is a perspective, cross-sectional, bottom view of the tracheostomy valve illustrated in FIG. 1.
Figure 8:
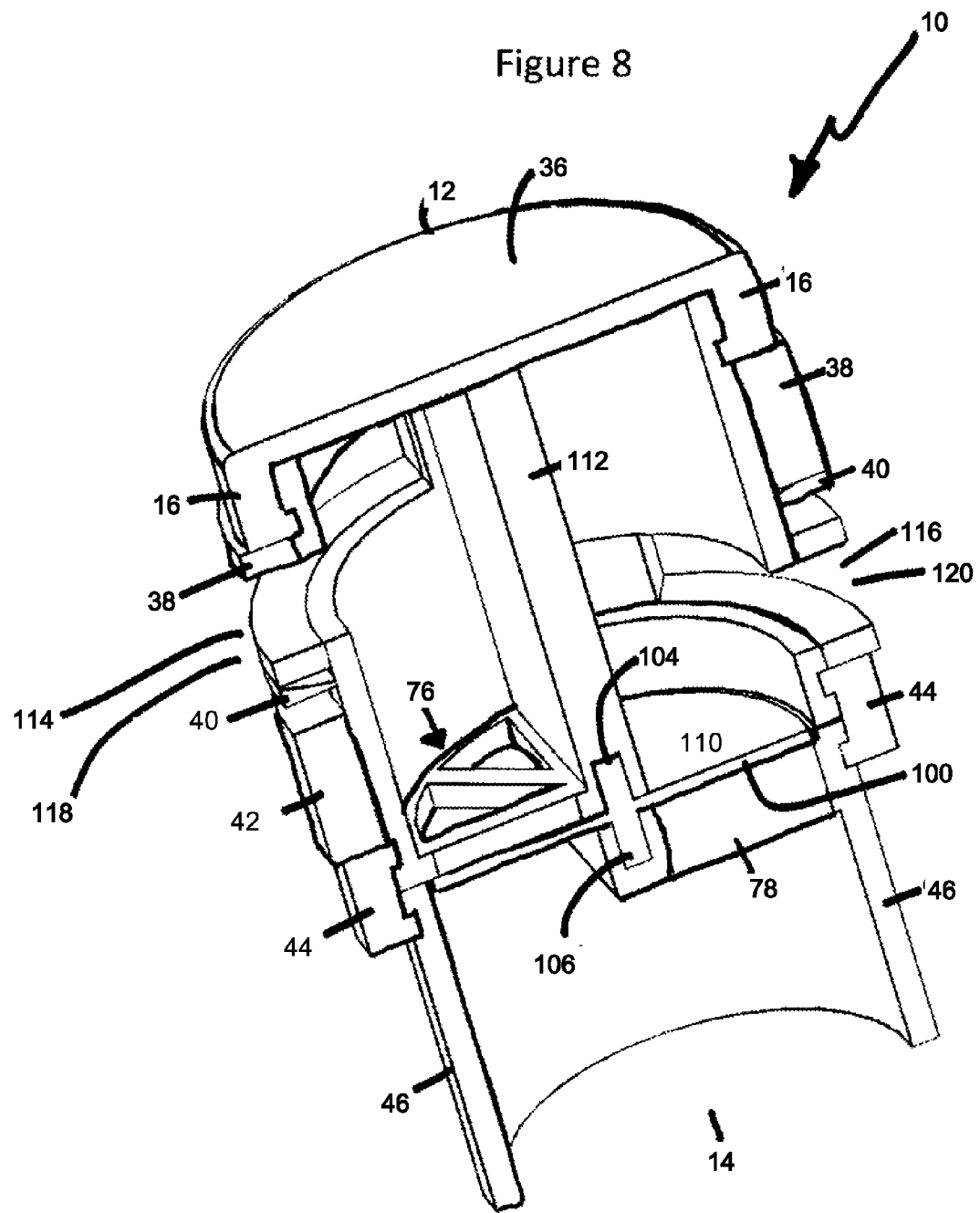
FIG. 8 is a perspective, cross-sectional, top view of the tracheostomy valve illustrated in FIG. 1.

With reference to FIGS. 7 and 8, the main barrel 20 and the trach barrel 46 are intended to but against one another. The main barrel 20 and the trach barrel 46, therefore, form the basic structure, or main body, of the valve 10 when assembled together.

As noted above, the trach barrel 46 is provided for coupling with a suitable tracheostomy tube, as should be apparent to those skilled in the art. The tracheostomy tube (not shown) is positioned within the patient's tracheostomy and is usually held in place via a strap or other securement that extends around the person's neck.

Figure 6:
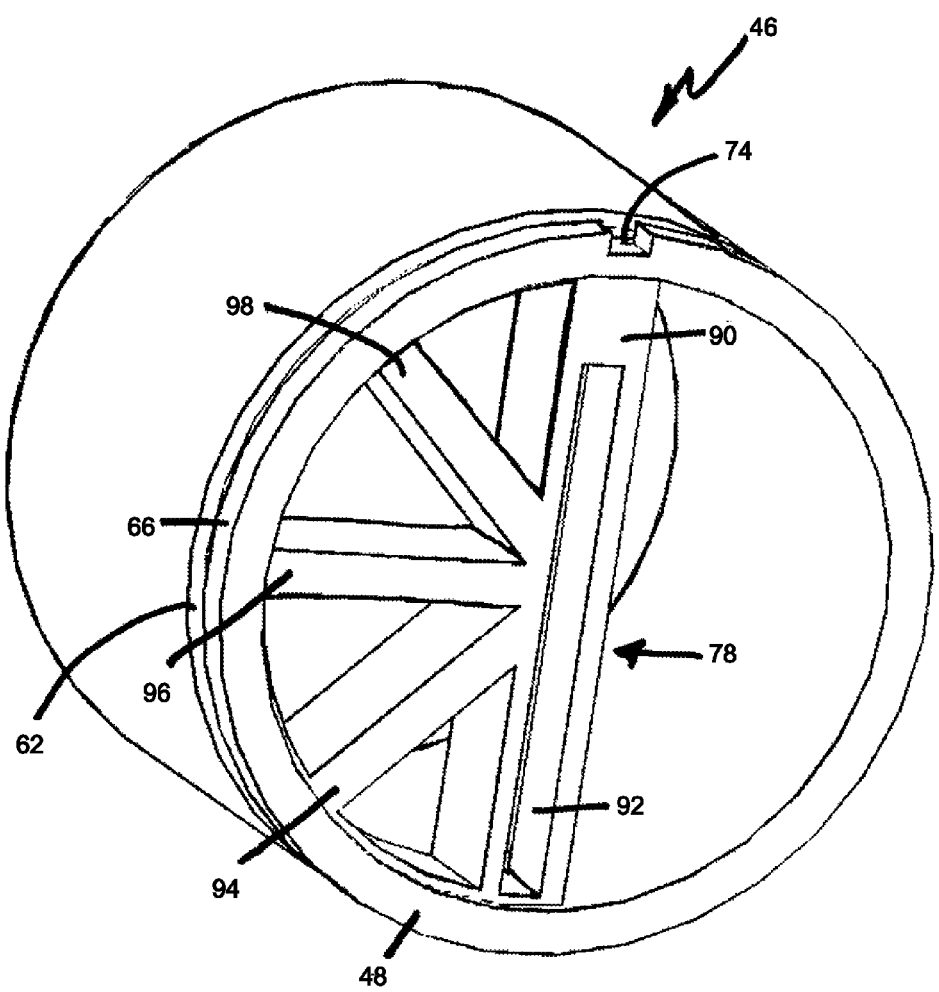
FIG. 6 is a perspective, top view of the trach barrel portion of the tracheostomy valve illustrated in FIG. 1.

FIG. 6 is a perspective illustration of the trach barrel 46. The trach barrel 46 has a top (or distal) end 48 and a bottom (or proximal) end 50. The top end 48 of the trach barrel 46 mates with the bottom end 22 of the main barrel 20. In the illustrated embodiment, the coupling ring 44 connects the trach barrel 46 to the main barrel 20. The bottom end 50 of the trach barrel 46 mates with the tracheostomy tube (not shown).

Figure 11:
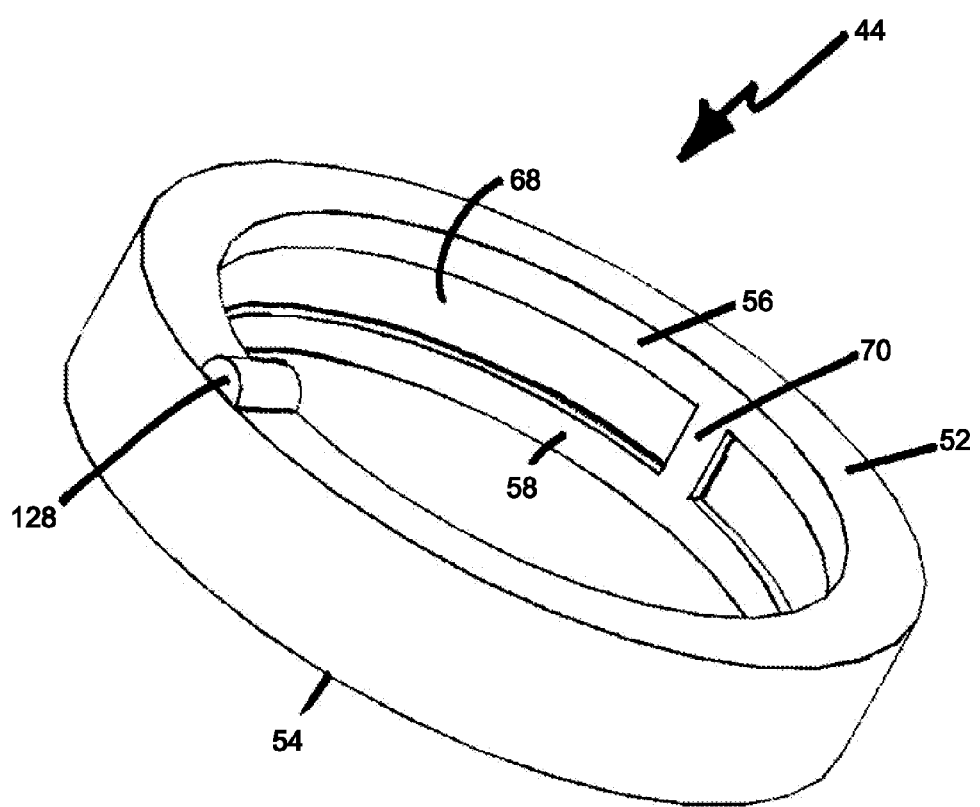
FIG. 11 is a perspective, top view of the coupling ring portion of the tracheostomy valve illustrated in FIG. 1.

Reference is now made to FIG. 11, which provides a perspective illustration of the coupling ring 44. The coupling ring 44 is essentially a cylindrical ring with a top end 52 and a bottom end 54. A top locating ring 56 is positioned on the interior surface of the coupling ring 44 at the top end 52. A bottom locating ring 58 is positioned on the interior surface of the coupling ring 44 at the bottom end 54. The top locating ring 56 mates with a locating channel 60 on the exterior surface at the bottom end 22 of the main barrel 20. The bottom locating ring 58 mates with a locating channel 62 at the top end 48 of the trach barrel 46.

As also should be apparent from FIGS. 4 and 6, the main barrel 20 includes a locating ring 64 at its bottom end 22. The trach barrel 46 includes a locating ring 66 at its top end 48. When positioned adjacent to one another, the locating ring 64 on the main barrel 20 and the locating ring 66 on the trach barrel 46 collectively form a single locating ring that is received within the locating channel 68 on the interior surface of the connecting ring 44.

As shown in FIG. 11, a locating ridge 70 is disposed on the interior surface of the coupling ring 44. The locating ridge 70 extends between the top locating ring 56 and the bottom location ring 58.

With reference to FIGS. 4 and 6, the main barrel 20 includes a locating recess 72 at the bottom end 22. Similarly, the trach barrel 46 includes a locating recess 74 at its top end 48. When the bottom end 22 of the main barrel 20 is positioned adjacent to the top end 48 of the trach barrel 46, the locating recesses 72, 74 are aligned with one another to form a single locating recess. The locating ridge 70 on the interior surface of the coupling ring 44 engages the locating recesses 72, 74, which prevents the coupling ring 44 from rotating with respect to the main barrel 20 and the trach barrel 46. In addition, cooperation between the locating ridge 70 on the coupling ring 44 and the locating recesses 72, 74 hold the main barrel 20 in a fixed relationship to the trach barrel 46. In other words, the main barrel 20, the trach barrel 46, and the coupling ring 44 are constructed so that they cannot rotate with respect to one another.

While a single locating ridge 70 and locating recesses 72, 74 are described in connection with the coupling ring 44, a larger number may be employed without departing from the scope of the present invention.

As should be apparent, the coupling ring 44 is similar to the cap 16, except that the coupling ring 44 does not include a closed end 36. Similarly, the coupling ring 44 is contemplated to be made from a flexible material so that the coupling ring 44 may be slid over either one of the main barrel 20 or the trach barrel 46 until that the locating rings 64, 66 engage the locating channel 68 and until the locating rings 56, 58 engage the locating channels 60, 62.

It is noted that the coupling ring 44 and the cap 16 may be constructed from the same base element. Specifically, since the cap 16 differs from the coupling ring 44 in that it includes the closed end 36, it is contemplated that a single mold may be used to construct both the cap 16 and the coupling ring 44. Once manufactured, the cap 16 may be completed by adding the closed end 36 to the top end. The closed end 36 may be adhered to the cap 16 via any suitable means including, but not limited to, adhesive, thermal welding, sonic welding, or the like.

When the valve 10 is assembled, the bottom end 22 of the main barrel 20 is positioned adjacent to the top end 48 of the trach barrel 46. As a result, the locating rings 64, 66 abut against one another. Together, the two locating rings 64, 66, therefore, establish a single locating ring that engages the locating channel 68, which is defined on the interior surface of the coupling ring 44.

When the main barrel 20 and the trach barrel 46 are disposed in the proper orientation with respect to one another, the locating recess 72 on the main barrel 20 will be in register with the locating recess 74 on the trach barrel 46. Together, the locating recesses 72, 74 engage the locating ridge 70 on the interior surface of the coupling ring 44. The locating ridge 70 cooperates with the locating recesses 72, 74 to prevent the locking ring 44 from rotating with respect to the main barrel 20 and the trach barrel 46.

As may be apparent, the coupling ring 44 is intended to be made from a material that is suitably flexible to be slide over either the main barrel 20 or the trach barrel 46, until the coupling ring 44 engages the locating channels 60, 62 and the locating recesses 72, 74.

As also is apparent from FIG. 4, the main barrel 20 includes a valve stop 76 at its bottom end 22. Similarly, as shown in FIG. 6, the trach barrel 46 includes a valve stop 78 at its top end 48. The valve stops 76, 78 are similar to one another in their respective constructions.

The valve stop 76 includes a central support 80 that extends across the interior diameter (or width) of the main barrel 20, bisecting the main barrel 20 into two separate halves. The central support 80 includes a positioning channel 82 therein, the purpose of which is discussed in greater detail below. Three radial supports 84, 86, 88 extend from a center point on the central support 80

Similarly, the valve stop 78 at the top end 48 of the trach barrel 46 includes a central support 90. The central support 90 extends across the interior diameter (or width) of the trach barrel 46 and bisects the cross-sectional area of the interior passage in the trach barrel 46. The central support 90 includes a positioning channel 92 therein. The valve stop 78 also includes three radial supports 94, 96, 98 that extend to the interior periphery of the trach barrel 46 from a center point on the central support 90.

Figure 13:
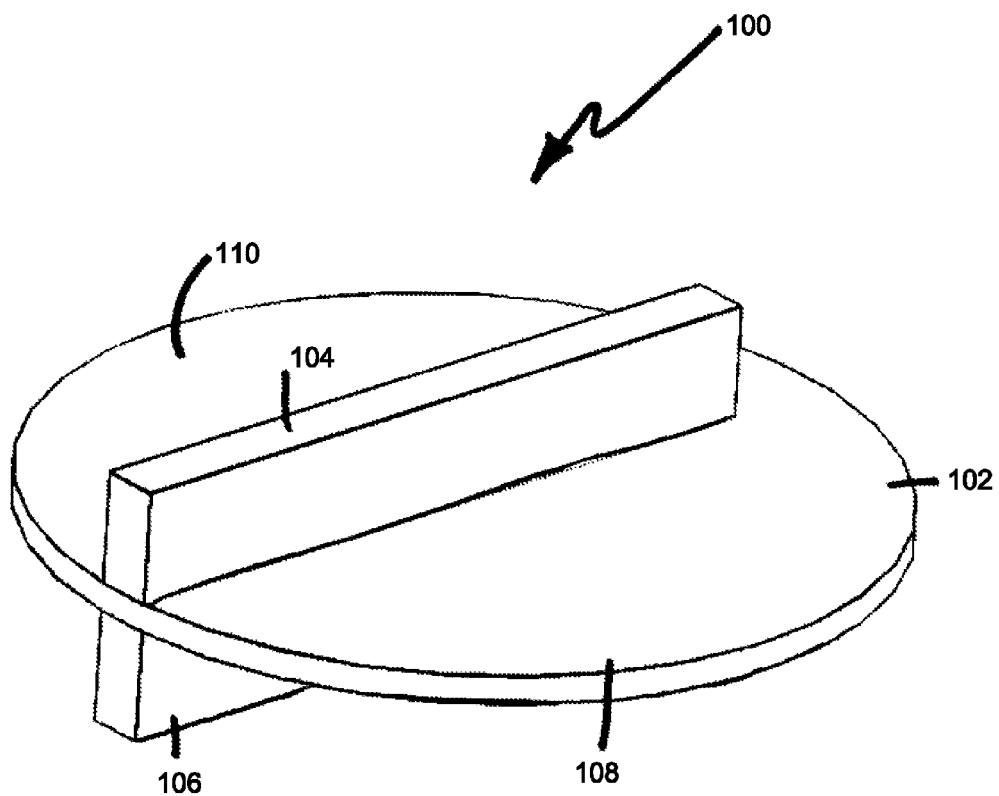
FIG. 13 is a perspective, top view of the flapper valve portion of the tracheostomy valve illustrated in FIG. 1.

The valve stops 76, 78 are positioned oppositely from one another within the valve 10. The valve stops 76, 78 are provided to inhibit movement of a flapper valve 100, which is illustrated in FIG. 13.

The flapper 100 includes a valve disk 102. The valve 100 includes a top positioning ridge 104 and a bottom positioning ridge 106. The top positioning ridge 104 is in register with the bottom positioning ridge 106. The positioning ridges 104, 106 effectively divide the flapper valve 100 into two equally-sized lobes 108, 110.

It is contemplated that the valve 100 will be constructed from a suitably flexible material such that the lobes 108, 110 are sufficiently flexible to bend in response to the inhalation and exhalation of the person using the valve 10 of the present invention. In one embodiment, the flapper valve 100 may be made from a silicone rubber. Other contemplated embodiments encompass other types rubbers, plastics, etc. The exact composition of the flapper valve 100 is not critical to the operation of the flapper valve 100. Accordingly, any suitable material may be employed without departing from the scope of the present invention.

With respect to the ridges 104, 106, it is contemplated that the ridges 104, 106 will be made from the same material as the valve disk 102. Moreover, it is contemplated that the flapper valve 100 will be molded as an integral component. It is noted, however, that the ridges 104, 106 need not be molded together with the valve disk 102. To the contrary, the ridges 104, 106 made be made from a different material and may be attached to the valve disk 102 in any manner, as should be understood by those skilled in the art.

The flapper valve 100 is sandwiched between the bottom end 22 of the main barrel 20 and the top end 48 of the trach barrel 46. The top positioning ridge 104 fits within the positioning channel 82 in the main barrel 20. The bottom positioning ridge 106 fits within the positioning channel 92 in the trach barrel 46. When the trach barrel 46 and the main barrel 20 are assembled together, therefore, the flapper valve 100 is held securely between the main barrel 20 and the trach barrel 46.

When the main barrel 20, the trach barrel 46, and the flapper valve 100 are assembled together, the lobe 108 is positioned to be seated against the valve stop 76. Similarly, the lobe 110 is seated against the valve stop 78. As will be discussed in greater detail below, the valve stops 76, 78 prevent the flapper valve 100 from opening in one direction. However, the valve stops 76, 78 do not interfere with the opening of the flapper valve 100 in the opposite direction.

As should be apparent from the various figures of the drawings, the valve stop 76 is positioned on one side of the valve 10 and the valve stop 78 is positioned on the other side of the valve 10.

With continued reference to FIGS. 4 and 5, the main barrel 20 includes a central wall 112 that extends from the top end 18 to the bottom end 22. Near the top end of the main barrel 20, a top aperture 114 extends through the side wall. The top aperture 114 is rectangularly shaped and extends around the periphery of the exterior wall of the main barrel 20, on one side of the central wall 112. A bottom aperture 116 is provided near the bottom end 22 of the main barrel 20. The bottom aperture 116 also is rectangularly shaped and extends around the periphery of the exterior wall of the main barrel 20, on the opposite side of the central wall 112 from the top aperture 114. As is apparent, the first and second apertures 114, 116 do not extend a full 180° around the periphery of the main barrel 20. To the contrary, they extend a length smaller than 180°, at least due to the presence of the central wall 112.

With respect to the first and second apertures 114, 116, a rectangular shape is not required to practice the present invention. To the contrary, the first and second apertures 114, 116 may be of any shape, as required or as desired, without departing from the scope of the present invention.

As should be apparent, the coupling ring 44 and the cap 16 define a region therebetween where a substantial portion of the main barrel 20 is exposed. The first adjustment ring 38, the spring ring 40, and the second adjustment ring 42 occupy the space between the cap 16 and the coupling ring 44. The first adjustment ring 38, the spring ring 40, and the second adjustment ring 42 extend around the outside surface of the main barrel 20, between the cap 16 and the coupling ring 44.

As will be made apparent from the discussion that follows, the cap 16, the main barrel 20, the coupling ring 44, and the trach barrel 46 are fixed in relation to one another. In other words, once assembled into a single unit, these elements cannot rotate with respect to another. While a fixed positioning of these elements is contemplated for one or more embodiments of the present invention, other embodiments are contemplated where the elements are not fixed in relation to one another, as should be apparent to those skilled in the art.

In this contemplated embodiment of the valve 10, the first adjustment ring 38, the spring ring 40, and the second adjustment ring 42 are permitted to rotate about the main barrel 20. As such, the first adjustment ring 38, the spring ring 40, and the second adjustment ring 42 are rotatable with respect to the cap 16, the main barrel 20, the coupling ring 44, and the trach barrel 46.

As illustrated in FIG. 1, the first adjustment ring 38 includes a first aperture 118 therethrough. The first aperture 118 is rectangularly shaped, like the first aperture 114 in the main barrel 20. Similarly, the second adjustment ring 42 includes a second aperture 120 therethrough. The second aperture 120 is rectangularly shaped, like the second aperture 116 in the main barrel 20. The first apertures 114, 118 are in register with one another and cooperate to define a first adjustable opening. Similarly, the second apertures 116, 120 are in register with one another and cooperate to define a second adjustable opening. The first adjustable opening 114, 118 is provided on the inhalation side of the valve. The second adjustable opening 116, 120 is provided on the exhalation side of the valve 10.

As noted above, the rectangular shape of the apertures 114, 116, 118, 120 is not critical to operation of the present invention. To the contrary, any shape may be employed without departing from the scope of the present invention. In addition, while each of the apertures 114, 116, 118, 120 are the same shape, it is not necessary for the apertures 114, 116, 118, 120 to have the same shape. Each of the apertures 114, 116, 118, 120 may have different shapes without departing from the scope of the present invention.

The first adjustment ring 38 is provided with a plurality of first adjustment notches 122 in a top edge thereof. The second adjustment ring 42 includes a plurality of second adjustment notches 124 along the bottom edge thereof. The first adjustment notches 122 are provided to engage the first protrusion 126 on the bottom edge of the cap 16. The second adjustment notches 124 engage the second protrusion 128 on the top edge of the coupling ring 44.

The adjustment rings 38, 42 are positioned on the valve 10 so that they may be rotated with respect to the main barrel 20. The notches 122, 124 and protrusions 126, 128 hold the adjustment rings 38, 42 in selected positions with respect to the main barrel 20. As noted above, the cap 16 is held in a non-rotating position at the top end 18 of the main barrel 20. Similarly, the coupling ring 44 is held in a non-rotating position at the bottom end 22 of the main barrel 20. Since the cap 16 and the coupling ring 44 are fixed in place, so are the protrusions 126, 128.

When either of the first or second adjustment rings 38, 42 are rotated, the protrusions 126, 128 engage one of the notches 122, 124. As such, the first and second adjustment rings 38, 42 are held in place.

As should be apparent, when the first adjustment ring 38 is rotated, the first aperture 118 in the adjustment ring 38 is shifted with respect to the first aperture 114 in the main barrel 20. As a result the first opening defined by cooperation between the first apertures 114, 118 may be made larger or smaller, as required or as desired. Similarly, the second apertures 116, 120 may be shifted in position with respect to one another to alter the size of the resulting second opening defined thereby. In this manner, as discussed in greater detail below, the rate of air flow through the valve 10 may be regulated and/or adjusted, as required or desired.

One aspect of the present invention lies in the fact that the first adjustment ring 38 and the second adjustment ring 42 are actually the same component. When installed on the valve 10, only the orientations of the rings 38, 42 differ from one another.

Figure 12:
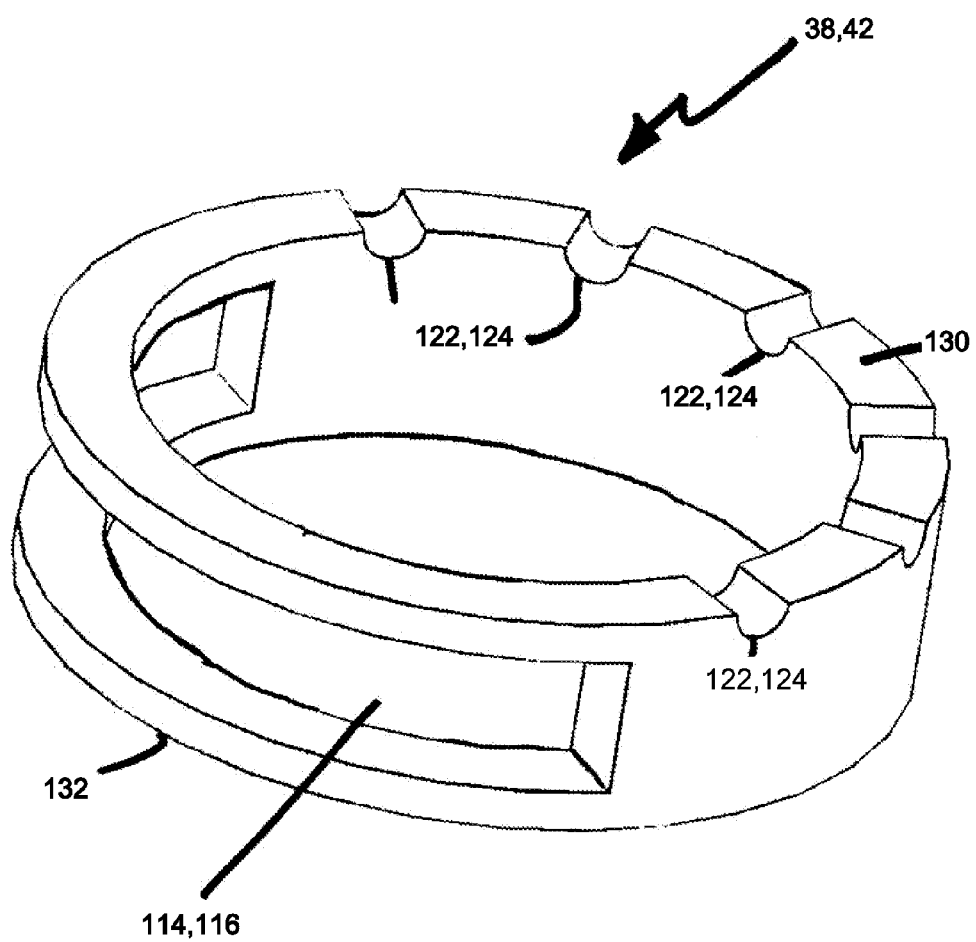
FIG. 12 is a perspective, top view of the adjustment ring portion of the tracheostomy valve illustrated in FIG. 1.

Because the adjustment rings 38, 42 are the same structure, only a single detailed view of the rings 38, 42 is provided in FIG. 12. The aperture 114, 116 in the ring 38, 42 is clearly shown, as are the adjustment notches 122, 124. To facilitate discussion of the spring ring 40, the top edge 130 of the rings 38, 42 is designated in addition to the bottom edge 132.

Figure 14:
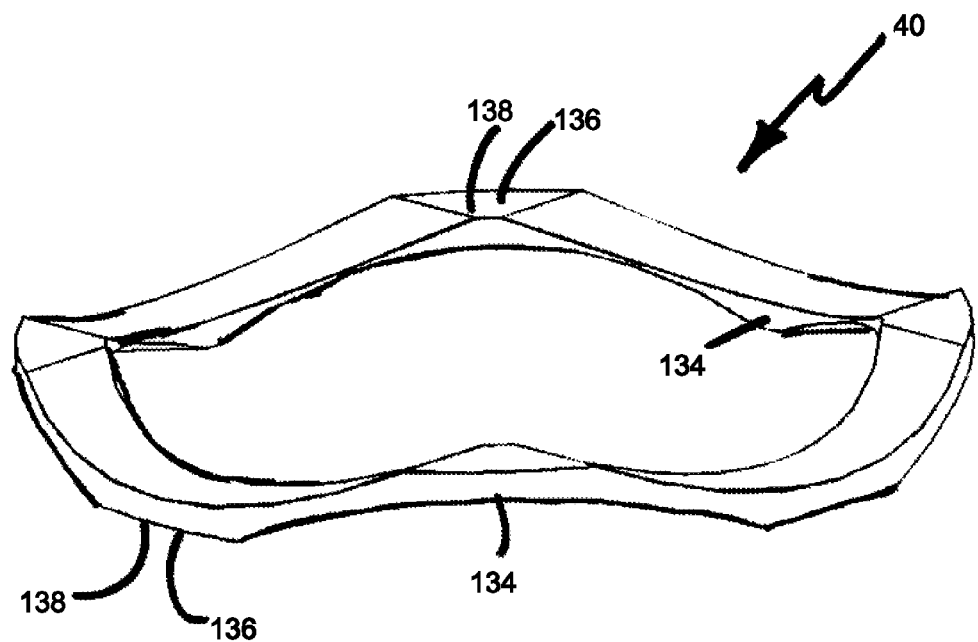
FIG. 14 is a perspective, top view of the spring ring portion of the tracheostomy valve illustrated in FIG. 1.

The spring ring 40 is illustrated in detail in FIG. 14. The spring ring 40 is positioned between the adjustment rings 38, 42. As illustrated in FIG. 1, for example, the spring ring 40 abuts against the bottom edges 132 of the adjustment rings 38, 42. With this arrangement, the adjustment notches 122, 124 at the top edge 130 of the adjustment rings 38, 40 are able to engage the protrusions 126, 128.

The spring ring 40 biases the adjustment rings 38, 42 into pressing engagement with the cap 16 and the coupling ring 44. Since the spring ring 40 is flexible, when either of the adjustment rings 38, 42 are rotated, the rings 38, 42 are able to move axially against the pressure of the spring ring 40, thereby permitting the protrusion 126, 128 to be moved to different adjustment notches 122, 124. As a result, the apertures 118, 120 may be opened or closed to any degree, as required or desired.

The spring ring 44 is contemplated to be made from a material such as plastic, nylon, polytetrafluoroethylene, or other suitable material that provides sufficient rigidity and flexibility for the spring ring 44 to hold the adjustment rings 38, 42 in place. While plastics and polymers are anticipated to be the materials of choice, the spring ring 44 may be made from any suitable material including metal, metal alloys, and composite materials, among others, without departing from the scope of the present invention.

In addition, it is noted that the spring ring 44 may be omitted from the valve 10 of the present invention altogether. In such an embodiment, it is contemplated that the adjustment rings 38, 42 may be provided with biasing means that would serve the function of the spring ring 44. Still further embodiments are contemplated to fall within the scope of the present invention.

With reference to FIG. 14, the spring ring 44 is essentially a cylindrical structure with an inside diameter that is greater than the outside diameter of the main barrel 20. As such, like the adjustment rings 38, 42, the spring ring 44 slides over the main barrel 20 but is not directly connected to the main barrel 20.

The spring ring 44 is essentially a flexible structure with a plurality of undulations 134. The tops and/or bottoms 136 of the undulations are provided with flat surfaces 138 that facilitate engagement with the bottom edges 132 of the adjustment rings 38, 42. It is noted that the flat surfaces 138 are not required to practice the present invention.

As will be appreciated by those skilled in the art, a number of springs or other types of biasing devices may be utilized instead of the spring ring 44. Examples include, but are not limited to, compression springs, and elastomeric materials (including resilient O-rings or flat washers).

Figure 15:
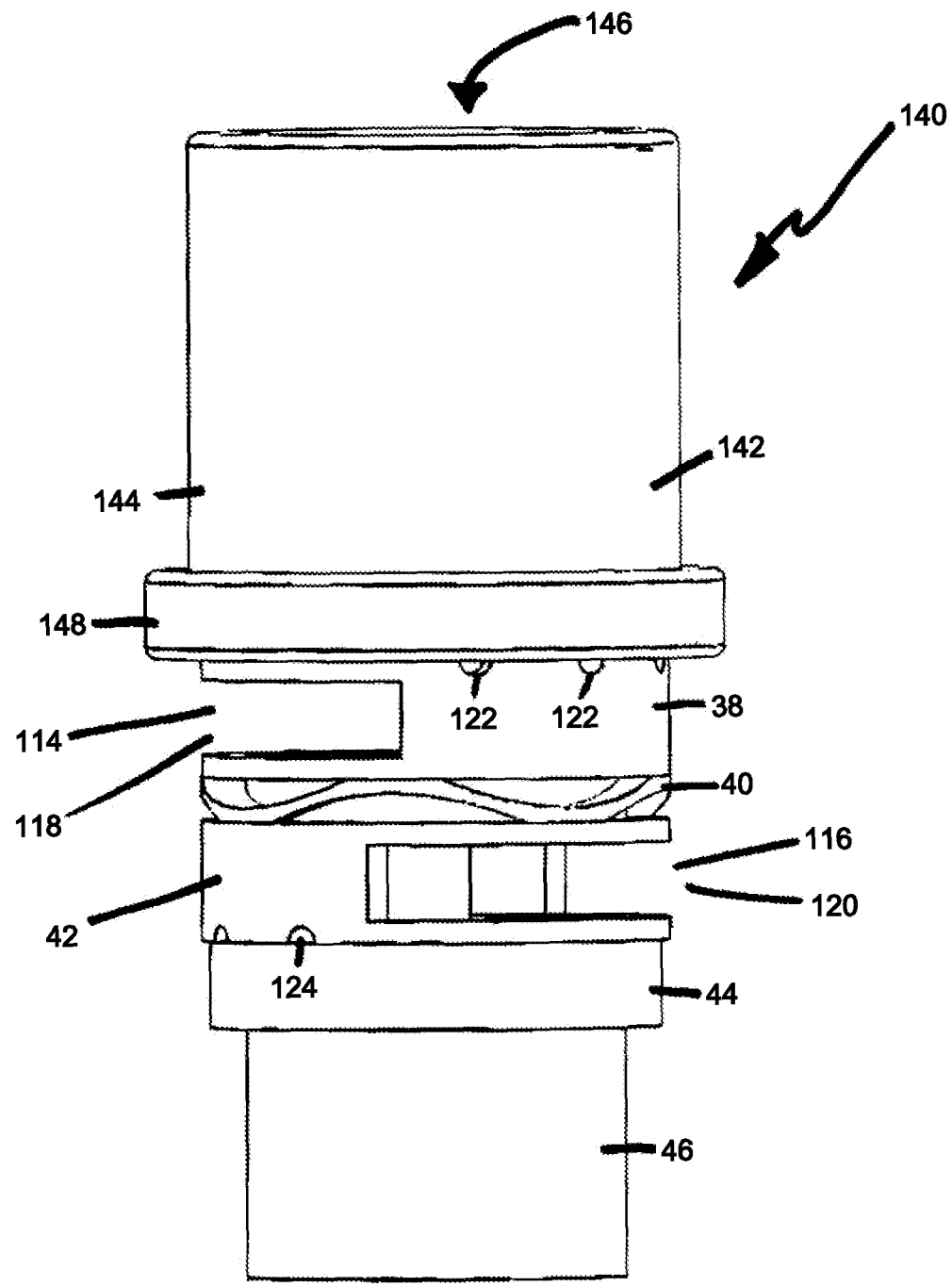
FIG. 15 is a side view of a second embodiment of a tracheostomy valve of the present invention.
Figure 16:
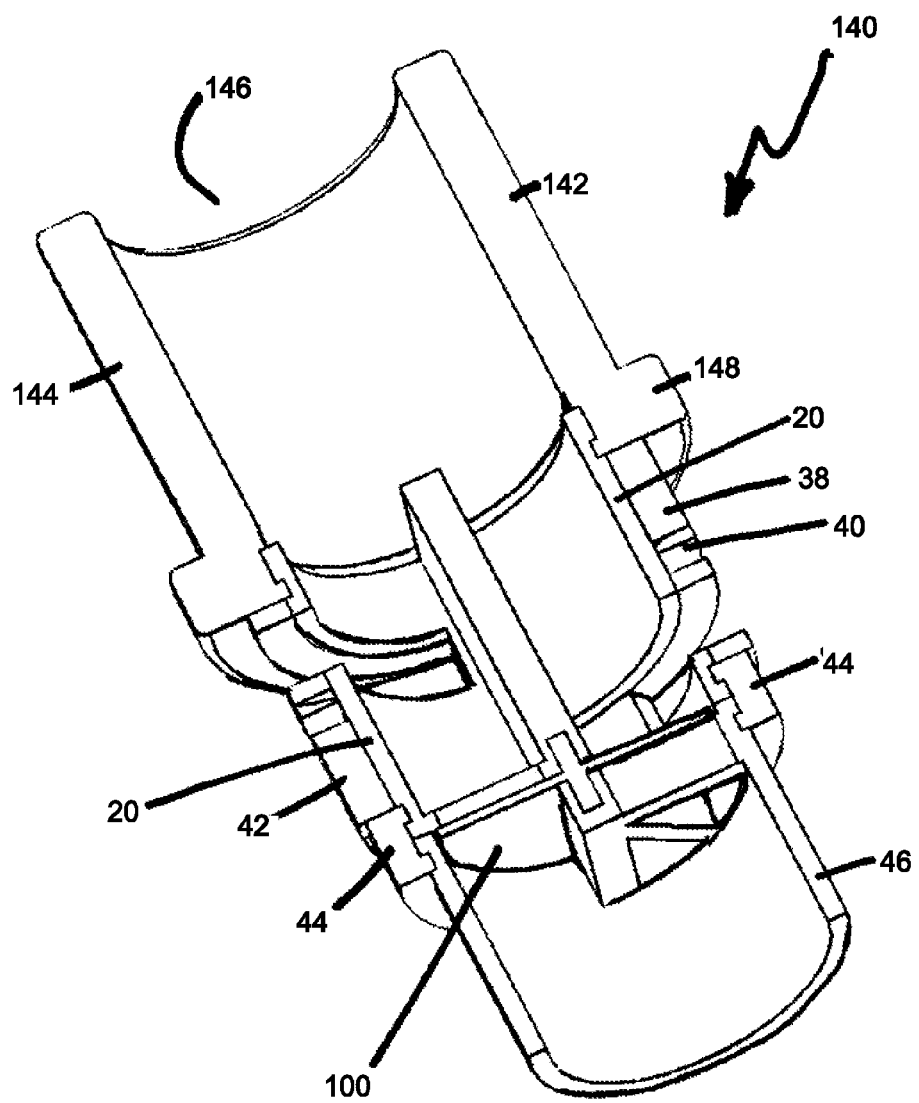
FIG. 16 is a perspective, cross-sectional, bottom view of the tracheostomy valve illustrated in FIG. 15.
Figure 17:
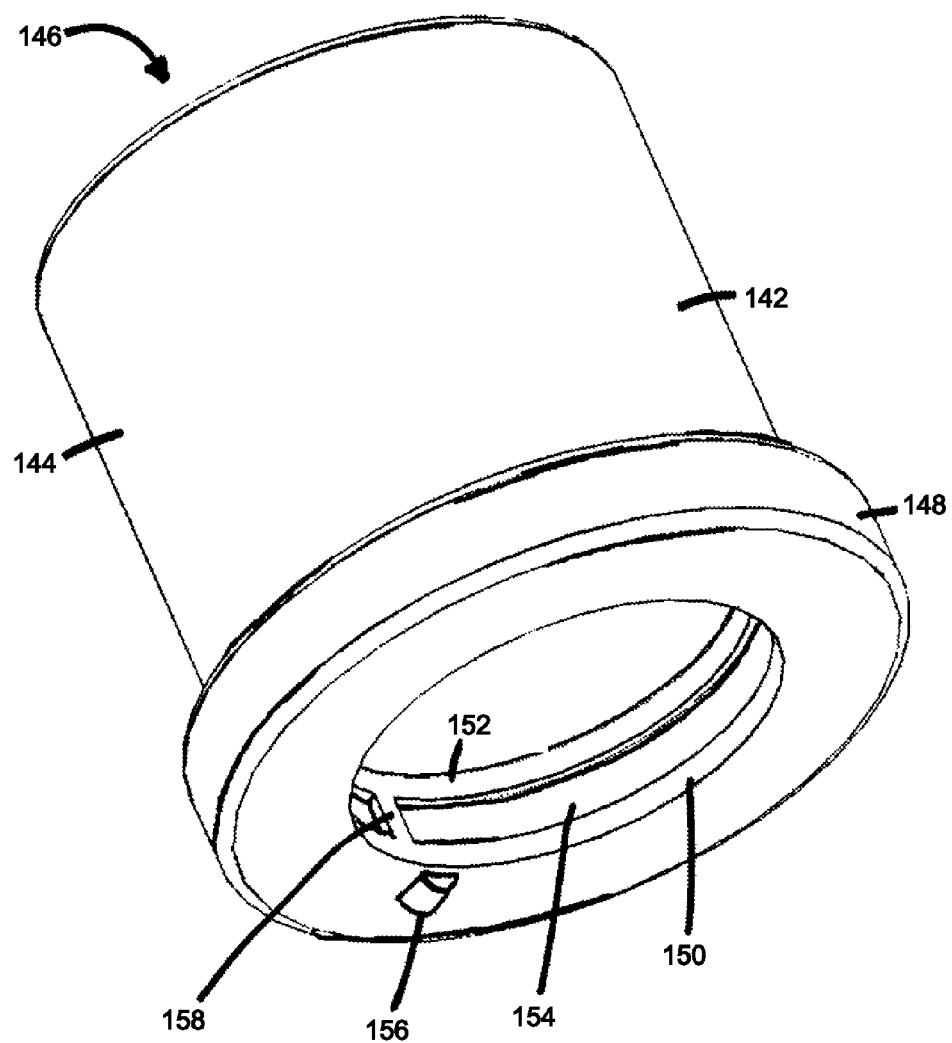
FIG. 17 is a perspective, bottom view of the cap portion of the tracheostomy valve illustrated in FIG. 15.

Reference is now made to FIGS. 15-17, which illustrate a second contemplated embodiment of a valve 140 according to the present invention.

The valve 140 is essentially the same as the valve 10 described above. Accordingly, for brevity, like reference numbers for the valve 10 are employed for like structures of the valve 140. Moreover, the materials employed for the components of the valve 140 are the same as discussed above with respect to the valve 10.

The difference between the valve 10 and the valve 140 lies in the design and construction of the cap 142 for the valve 140. Instead of being a cap 16 with a closed end 36, the cap 142 of the valve 140 has an opened end that is designed to receive a tube from a respirator or ventilator, which provides forced air flow. Moreover, the cap 142 is constructed to be exchangeable with the cap 16 from the valve 10.

As shown in FIGS. 15-17, the cap 142 has a cylindrical coupling portion 144 at its top end with an open end 146. A coupling ring 148 is integrally formed at the bottom end of the cap 142.

As illustrated in FIG. 17, for example, the coupling ring 148 includes two locating rings 150, 152 and a locating channel 154. The cap 142 also includes the protrusion 156 and a locating ridge 158. The locating rings 150, 152 and locating channel 154 engage the locating ring 30 and the locating channel 28 at the top 18 of the main barrel 20. The locating ridge 158 engages the locating recess 26 on the main barrel 20. The protrusion 156 engages the adjustment notches 122 on the first adjustment ring 38.

With the exception of the open end 146, the cap 142 operates in the same manner as the cap 16 on the valve 10.

With reference to the materials that may be employed for the various embodiments of the present invention, it is noted that the components may be treated or may incorporate one or more materials designed to improve the wearability of the device containing the valve. For example, the valve 10 may be made from a material that incorporates silver, copper, or other substances that enhance the antibacterial properties of the materials. The valve 10 may be made from, be coated with, or incorporate other substances that enhance other aspects of the device. The scope of the present invention is intended to encompass these materials as well.

Additional details concerning aspects of the valves 10, 140 of the present invention are provided below.

With renewed reference to FIG. 13, it is contemplated that the flapper valve 100 will be constructed with s symmetric shape and design. As a result, the flapper valve 100 does not have a top end or a bottom end. In other words, the flapper valve 100 operates in the same manner regardless of its orientation when sandwiched between the main barrel 20 and the trach barrel 46.

While a symmetrical construction is considered for the present invention, it is contemplated that the flapper valve 100 may have a non-symmetric construction. For example, the top and bottom positioning ridges 104, 106 need not be in register with one another. To the contrary, the positioning ridges 104, 106 may be offset from one another.

In the embodiments of the valve 10, 140 described above, the lobes 108, 110 of the flapper valve are contemplated to assert equal resistive forces when subjected to an air flow. In other words, the lobes 108, 110 are expected to bend to an equal degree (or to a substantially equal degree) when subjected to the same air flow and/or forces. It is for this reason, among others, that the flapper valve 100 is symmetric in its design.

One variation on this design contemplates that the lobes 108, 110 will not offer the same resistance to air flow. Instead, it is possible that the lobes 108, 110 may offer different resistances to air flow. For this variation, therefore, the flapper valve 100 will require placement in the valve 10, 140 in a particular orientation.

In connection with this variation, it is contemplated that the valve stops 76, 78 might present surfaces that are not perpendicular with respect to the walls of the main barrel 20 or the trach barrel 46. It is contemplated that the surfaces of the valve stops 76, 78 that touch the lobes 108, 110 of the flapper valve 100 may be angled with respect to the walls of the main barrel 20 or the trach barrel 46. This construction also is contemplated to provide a design that introduces variability in operation between the lobes 108, 110 of the flapper valve 100.

In still another contemplated embodiment, the passages within the main barrel 20 need not be of equal cross-sectional size. With different cross-sectional areas, the passages are anticipated to offer different air flow resistances, which alters the operation of the valve 10, 140 with such a construction.

Still further, it is noted that the flapper valve 100 is contemplated to be made from a singular material, such as silicone rubber, for example. If it is desired to vary the resistance offered by the lobes 108, 110 of the flapper valve 100, it is contemplated that the lobes 108, 110 may be altered in their composition. For example, one lobe 108, 110 might be made to be thicker than the other or may include stiffening ribs. Alternatively, the lobes 108, 110 might be made from different materials or combinations of materials. Still other variations are contemplated to fall within the scope of the present invention.

As discussed above, the adjustment rings 38, 42 are maintained in a rotational location via interaction between the protrusions 126, 128 and the adjustment notches 122, 124. Other adjustment mechanisms may be employed for the valves 10, 140 without departing from the scope of the present invention. In one contemplated embodiment, a series of interlocking teeth might be employed. The teeth might be arranged in a saw tooth pattern, for example. Alternatively, the surfaces that are in contact with one another might be provided with frictionally-interactive materials to discourage unintended movement of the adjustment rings 38, 42. For example, the top edges 130 of the adjustment rings 38, 42 might be provided with an abrasive layer and/or coating. Still further, the top edges 130 might be abraded to establish a sufficiently frictional surface to discourage rotation of the adjustment rings 38, 42 with respect to the main body 20.

In the embodiments of the valves 10, 140, the adjustment rings 38, 42 are provided with adjustment locking features (i.e., the projections 126, 128 and notches 122, 124) that apply forces in an axial direction. It is possible, in one contemplated embodiment, that the adjustment rings 38, 42 may be mounted such that the adjustment features require cooperation between the adjustment rings 38, 42 and the main barrel 20. In other words, the adjustment features may be radially aligned rather than being axially aligned, as discussed above.

Regardless of the orientation of the adjustment mechanism employed for the valve 10, 140 of the present invention, it is contemplated that the adjustment of the apertures 114, 116, 118, 120 with respect to one another will be achieved via discrete interval adjustments. It is for this reason that the projections 126, 128 and the notches 122, 124 are provided in the manner described above.

It is an object of the present invention to provide adjustability for the apertures 114, 116, 118, 120 so that the person wearing the valve 10, 140 or the practitioner assisting the person wearing the valve 10, 140 may alter the air flow through the valve 10, 140. There are a number of reasons for this, as should be apparent to those skilled in the art.

For example, as should be known to those skilled in the art, there are a number of different sizes of tracheostomy tubes that are available for practitioners and tracheostomy patients. Specifically, there are five standard tracheostomy tube sizes: 10 mm, 8 mm, 6 mm, 4 mm, and 2 mm. It is not uncommon for a patient to be transitioned from a larger tracheostomy tube to a smaller tracheostomy tube. At present, when the transition is made, the practitioner removes the larger tube and inserts a smaller tube. As should be apparent, if the patient does not tolerate the transition, there is a period of discomfort until the smaller tube is removed and the larger tube is reinserted.

The present invention permits the practitioner to evaluate if a person can tolerate a smaller tube by adjusting the apertures 114, 116, 118, 120 in the valve 10, 140 before removing the existing tracheostomy tube and inserting a smaller tube. In connection with the valves of the present invention, it is contemplated that the notches 122, 124 will be positioned on the adjustment rings 38, 42 such that they approximate the different sizes of tracheostomy tubes. Accordingly, the practitioner need only move the adjustment rings 38, 42 a single notch to approximate a change in the tracheostomy tube by one standard size. If the patient cannot tolerate the change, the practitioner need only readjust the adjustment rings 38, 42 to their prior settings.

As should be apparent to those skilled in the art, the valves 10, 140 may be modified to present a larger or smaller number of gradations. Moreover, as noted above, the valves 10, 140 of the present invention may be constructed to provide an infinite number of positions for the adjustment rings 38, 42, as required or as desired.

It is noted that the adjustability of the apertures 114, 116, 118, 120 also may be provided to assist the patient with breathing exercises, as might be appropriate or required for physical therapy, for example. Moreover, the valves 10, 140 are anticipated to assist new tracheostomy patients to tolerate the valves 10, 140.

As should be apparent to those skilled in the art, when a patient first receives a tracheostomy tube, the patient typically does not begin with any type of valve that redirects exhalation air through the person's throat to permit the person to speak. Such valves are known as phonating valves.

Typical phonating valves permit inhalation as force all exhalation through the person's throat, thereby permitting activation of the vocal chords. The present invention provides adjustability of the exhalation path such that only a portion of the exhalation is directed over the vocal chords. It has been found, for example, that some patients are unable to tolerate all of their exhalation air being directed through their throats, due to their particular physical condition. By adjusting apertures 114, 116, 118, 120 associated with exhalation, it is possible to make the tracheostomy valve more comfortable for those patients.

Figure 9:
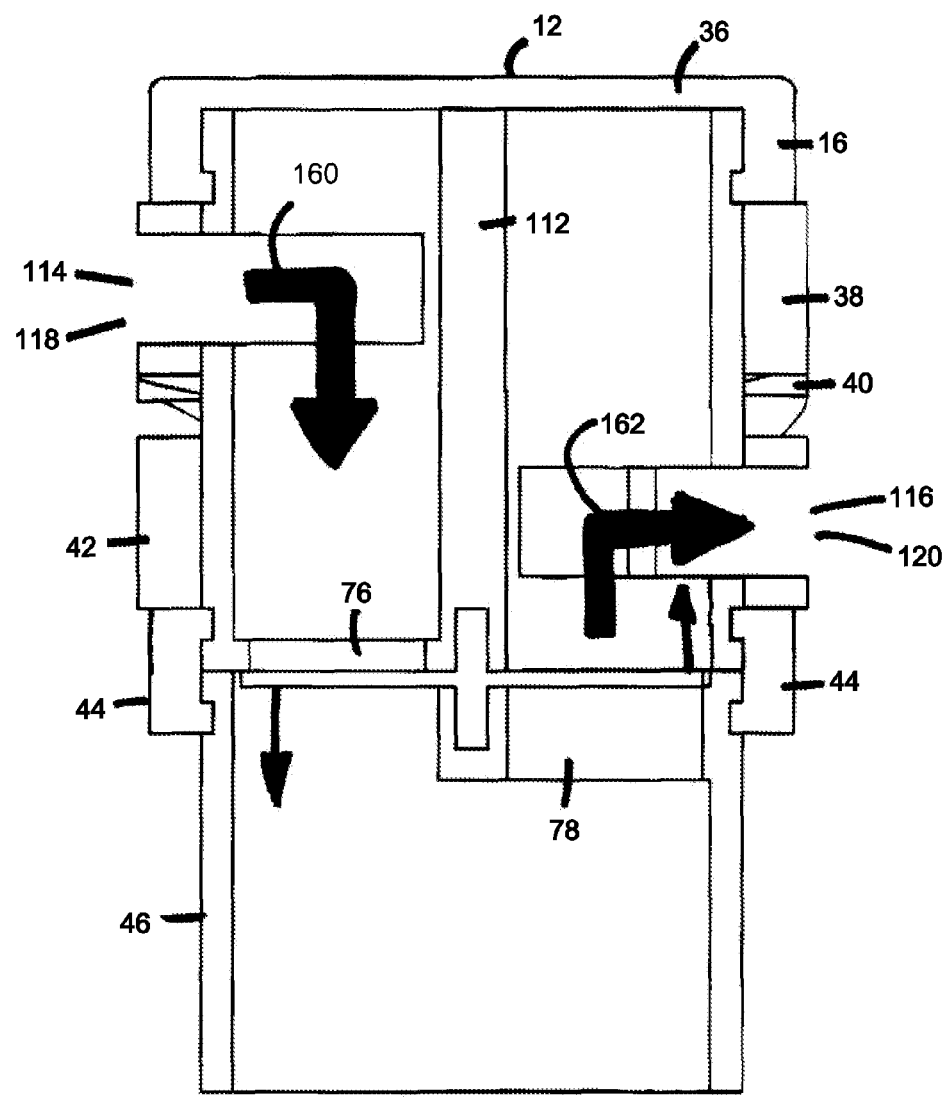
FIG. 9 is a cross-sectional side view of the tracheostomy valve illustrated in FIG. 1.

As should be apparent from the foregoing, the valves 10, 140 of the present invention permit adjustment of both the inhalation and exhalation air for different purposes. FIG. 9 is particularly helpful in appreciating how the valves 10, 140 of the present invention operate. For discussion purposes, FIG. 9 shows the valve 10. However, the operational discussion applies equally to the valve 140, as should be apparent to those skilled in the art.

The adjustment ring 38, which controls the orientation between the apertures 114, 118, provides control over a person's inhalation. The arrow 160 indicates the direction of the inhalation of air. The adjustment ring 42, which controls the orientation between the apertures 116, 120, provides control over the person's exhalation. The arrow 162 indicates the direction of the exhalation air.

As noted above, it may be necessary to adjust the flow of the exhalation air to permit some air to pass through the valve 10, 140 while the remaining exhalation air passes over the person's vocal chords, permitting speech. For example, due to the patient's physical condition, the patient may not be able to tolerate the entirety of the exhalation air being forced through the person's throat. To reduce this pressure, the valve 10, 140 is adjusted to permit some exhalation air to exit therethrough.

In general, the adjustable tracheostomy weaning and phonating valves consistent with the present invention will be configured for: (1) allowing bi-directional flow of air through the tracheostomy with the adjustable tracheostomy weaning and phonating valves in place; (2) controlling fluid flow within the adjustable tracheostomy weaning and phonating valves; and (3) providing an adjustable threshold, either constant or variable, through the phases of breathing on both inspiration and expiration.

Any and all variations to the designs disclosed herein that accomplish these three functions are considered to be within the scope of this disclosure. For example, the inspiration and expiration channels of the adjustable tracheostomy weaning and phonating valves 10, 140 may be provided on opposite legs of a "Y" or "T" valve configuration, additional overpressure valves may be provided to provide an enhanced flow for coughs and sneezes, ports may be provided for supplemental $O_2$, and/or additional structures may be provided for limiting movement of the flapper valve 100 to achieve a broader range of flow control. None of the variations, however, are considered to detract from the basic functionality of the disclosed adjustable tracheostomy weaning and phonating valve 10, 140. Accordingly, these variations are intended to be encompassed by the scope of the present invention.

The adjustable tracheostomy weaning and phonating valve 10, 140 may be used in several ways, as discussed above. As noted, the notches 122, 124 may be set to correspond to different tracheostomy tube sizes which simulate tube sizes starting at 10 mm and decreasing to 0 mm in increments of 2 mm. The adjustment rings 38, 42 allow the inspiratory flows as well as the expiratory flows to be completely and independently adjustable. It is noted that the 10 mm position is the most opened position available for the valve 10, 140 of the present invention. At this adjustment position, it is contemplated that the valve 10, 140 permits maximum air flow during both inspiration and exhalation.

As should be apparent from FIG. 9, the second adjustment ring 42 controls the expiratory flow of air through the valve 10, 140. Accordingly, it is anticipated that this adjustment ring 42 will be employed adjust the aperture 116, 120 over a period of time to acclimate the patient to the weaning and phonating valve 10, 140 of the present invention. As noted above, in the illustrated embodiments, the expiratory air flow may be adjusted from 10 to 0 in increments of 2 over a period of time. This permits the person to become used to the phonating aspect of the valve 10, 140 over that period of time.

As should be apparent, with the adjustment ring 38 set at 10 (inspiration) and the adjustment ring 42 (expiration) set at 0, the adjustable tracheostomy weaning and phonating valve 10, 140 allows the patient to inspire all of their tidal volume through the valve 10, 140, but forces all exhaled tidal volume to be forced out through the trachea, past the vocal cords, and out of the mouth and nose. Many of the patients do not tolerate a traditional speaking valve upon its initial installation. This may be due to vocal cord stenosis, tracheal or laryngeal swelling, or just do to anxiety from the increased work of breathing. With the adjustability provided by the valve 10, 140 of the present invention, the patient may be weaned "onto" the speaking valve. As the patient progresses and tolerates the valve 10, 140, the patient may progress beyond using the valve 10, 140 just for phonation and the traditional means.

The adjustable tracheostomy weaning and phonating valves 10. 140 may be used to wean the patient of off the tracheostomy tube all together by slowly closing the adjustment ring 38 (inspiration) as well. With the adjustment ring 42 (expiration) "closed" or set at "0," the adjustment ring (inspiration) can be weaned from "10" or wide open, down to "0" or "closed," thus being "capped." As the adjustment ring 38 is weaned or closed, the patient is forced to entrain more and more air through their natural airway.

The adjustable tracheostomy weaning and phonating valves 10, 140 eventually may have both adjustment rings 38, 42 "closed" or "capped." At this point, the valve 10, 140 and the tracheostomy tube may be removed altogether and the tracheostomy closed.

According to the present invention, with the adjustable tracheostomy weaning and phonating valve 10, 140 being fully adjustable, the patient may be weaned off of his or her tracheostomy tube in steps rather than going from a wide-open trach, to the traditional speaking valve, which presents a capped trach.

The valve 10, 140 of the present invention also allows the practitioner to test the patient to see if he or she is able to tolerate the downsizing of the tracheostomy tube, as indicated above. If the patient currently has a #8 tracheostomy tube in place and the physician wants to see if the patient can tolerate being downsized to a #6, both adjustment rings 38, 42 may be adjusted to the #6 setting, which simulates a #6 tracheostomy tube even though a #8 tube is in place. These adjustment settings may then be left in place for a predetermined period of time, for example, 24 hours. At the conclusion of the 24 hour period, the physician may have an ABG (Arterial Blood Gas) test done to determine if the smaller diameter tube has caused the patient to retain more $CO_2$ than is acceptable. It is noted that, when the adjustment rings 38, 42 are set at the #8 position, the same amount of air flow is permitted as would be available for a tracheostomy tube with an 8 mm ID. This is the equivalent of a Shiley 8DCT or a Portex #8 LPC.

With the explanation of the adjustable tracheostomy weaning and phonating valve 10, 140 above, the following benefits over the prior art may be realized. First, the patient should be able to tolerate the valve 10, 140 at any part of the phonating or weaning process because of complete adjustability. The prior art offers no adjustability on either inspiration or expiration. Second, the patient should be able to use the valve 10, 140 through the entire phonating or weaning process. Prior art valves require the patient to have both a phonating valve as well as a tracheostomy cap through the phonating and weaning processes. With the valve 10, 140 of the present invention, therefore, there is no need to switch from the speaking valve to a tracheostomy cap. Third, the valve 10, 140 of the present invention may be disassembled and reassembled, allowing for cleaning, sterilization and/or repair. Prior art valves do not offer this function. Fourth, the valve 10, 140 of the present invention may be used to test patient tolerance when it is questionable to downsize the size of a patient's tracheostomy.

The disclosure is not limited to the particular example embodiment of the adjustable tracheostomy weaning and phonating valve 10, 140 detailed above and illustrated in the corresponding drawings. As will be appreciated by those skilled in the art, various embodiments of adjustable tracheostomy weaning and phonating valve 10, 140 may be constructed that would still incorporate certain of the advantages and structures of the exemplary embodiments described herein.

The drawings and discussion herein are intended to illustrate the general characteristics of structures described in connection with the embodiments of the valve 10, 140 of the present invention. These drawings and description, however, should not be interpreted as defining or limiting the range of values or properties encompassed by the embodiments described herein. Moreover, as will be appreciated by those skilled in the art, there are many variations that could be made to the design detailed in the example embodiment that would accomplish the same results. For example, the materials selected for construction of the adjustable tracheostomy weaning and phonating valves could include any number of readily available polymers, ceramics and/or metals. Furthermore, a wide range of assembly structures, e.g., recesses and corresponding projections, set screws, welds, pins, etc., could easily be utilized for locating the various structural elements of the adjustable tracheostomy weaning and phonating valve 10, 140 of the present invention without departing from the basic functionality of the devices detailed herein.

What is claimed is:

1. A valve, comprising:
   a main body portion comprising
      a peripheral wall defining an interior space and an internal wall separating the internal space into first and second internal passages,
      a first aperture extending radially through the peripheral wall, connecting the first internal passage to an environment external to the main body, and
      a second aperture extending radially through the peripheral wall, connecting the second internal passage to the environment;
   a trach body portion disposed adjacent to the main body portion, the trach body portion defining a third internal passage;
   a flapper valve sandwiched between the main body portion and the trach body portion;
   a first adjustment ring having a third aperture therethrough, the first adjustment ring being disposed on the main body portion so that the third aperture is in register with the first aperture, the first adjustment ring being movable with respect to the main body portion to permit alteration of the positional relationship between the first and third apertures to alter a size of a first opening defined by the first and third apertures; and
   a second adjustment ring having a fourth aperture therethrough, the second adjustment ring being disposed on the main body portion so that the fourth aperture is in register with the second aperture, the second adjustment ring being movable with respect to the main body portion to permit alteration of the positional relationship between the second and fourth apertures to alter a size of a second opening defined by the second and fourth apertures.

2. The valve of claim 1, wherein:
   the first adjustment ring is rotatable with respect to the main body portion between an opened position, where the first and third apertures are aligned to permit a maximum air flow therethrough, and a closed position where the first and third apertures are not aligned to prevent air flow therethrough, and the second adjustment ring is rotatable with respect to the main body portion between an opened position, where the second and fourth apertures are aligned to permit a maximum air flow therethrough, and a closed position where the second and fourth apertures are not aligned to prevent air flow therethrough.

3. The valve of claim 2, wherein the first and second adjustment rings are adjustable to a predetermined number of discrete adjustment positions between the opened and closed positions.

4. The valve of claim 2, wherein the first and second adjustment rings are adjustable in any of an infinite number of adjustment positions between the opened and closed positions.

5. The valve of claim 1, further comprising:
a coupling ring disposed around a bottom end of the main body portion and a top end of the trach body portion, connecting the main body portion to the trach body portion so that the main body portion and the trach body portion do not rotate with respect to one another; and
a cap disposed at a top end of the main body portion such that the cap does not rotate with respect to the main body portion.

6. The valve of claim 5, wherein the cap further comprises:
a closed end, thereby requiring air passing through the first and second internal passages to flow through the first and second apertures.

7. The valve of claim 5, wherein the cap further comprises:
a coupling portion permitting coupling of the main body portion to a ventilator.

8. The valve of claim 5, further comprising:
at least one first protrusion disposed on a bottom edge of the cap for engagement with at least one first notch disposed along a top edge of the first adjustment ring to secure the first adjustment ring in a first predetermined position; and
at least one second protrusion disposed on a top edge of the coupling ring for engagement with at least one second notch disposed along a bottom edge of the second adjustment ring to secure the second adjustment ring in a second predetermined position.

9. The valve of claim 8, wherein:
the at least one first notch comprises a plurality of first notches, permitting the first adjustment ring to be secured in a plurality of first predetermined positions, and
the at least one second notch comprises a plurality of second notches, permitting the second adjustment ring to be secured in a plurality of second predetermined positions.

10. The valve of claim 9, wherein the plurality of first and second notches each comprise six notches, permitting the first and second adjustment rings to be secured in six predetermined positions corresponding to six tracheostomy tube sizes.

11. The valve of claim 10, wherein the six tracheostomy tube sizes comprise 10 mm, 8, mm, 6, mm, 4 mm, 2 mm, and 0 mm.

12. The valve of claim 8, further comprising:
a biasing element disposed between the first and second adjustment rings, biasing the first adjustment ring into engagement with the cap and also biasing the second adjustment ring into engagement with the coupling ring.

13. The valve of claim 12, wherein the biasing element is a spring ring.

14. The valve of claim 13, wherein the spring ring comprises a plurality of undulations and a plurality of flat surfaces, alternate ones of the flat surfaces being in contact with the first and second adjustment rings, respectively.

15. The valve of claim 1, further comprising:
a first valve stop disposed within the first internal passage, adjacent to the flapper valve; and
a second valve stop disposed within the third internal passage adjacent to the flapper valve.

16. The valve of claim 15, wherein:
the first valve stop cooperates with the flapper valve to permit air to flow through the first internal passage into the third internal passage during inhalation but prevents air from flowing from the third internal passage to the first internal passage during exhalation, and
the second valve stop cooperates with the flapper valve to permit air to flow through the second internal passage from the third internal passage during exhalation but prevents air from flowing from the second internal passage to the third internal passage during inhalation.

17. The valve of claim 1, wherein the first and second internal passages have substantially equal cross-sectional areas and the third internal passage has a cross-sectional area that is at least equal to the sum of the cross-sectional areas of the first and second internal passages.

18. The valve of claim 1, wherein the flapper valve comprises silicone rubber.

19. The valve of claim 1, wherein the trach body portion is connectable to a tracheostomy tube.

20. The valve of claim 19, wherein the valve facilitates phonation for a person by restricting exhalation air therethrough, thereby forcing at least a portion of the exhalation air through the person's vocal chords.

* * * * *